US005585239A

United States Patent [19]

Lamarco et al.

[11] Patent Number: 5,585,239
[45] Date of Patent: Dec. 17, 1996

[54] HERPES SIMPLEX VIRUS DRUG SCREEN

[75] Inventors: Kelly Lamarco, San Francisco, Calif.; Angus Wilson, Cold Spring Harbor; Winship Herr, Oyster Bay Cove, both of N.Y.

[73] Assignee: Tularik, Inc., San Francisco, Calif.

[21] Appl. No.: 393,703

[22] Filed: Feb. 24, 1995

Related U.S. Application Data

[60] Division of Ser. No. 46,585, Apr. 12, 1993, Pat. No. 5,453,362, which is a continuation-in-part of Ser. No. 989,842, Dec. 4, 1992, abandoned.

[51] Int. Cl.[6] .............................. C12Q 1/68; G01N 33/53
[52] U.S. Cl. ............................................ 435/6; 435/7.1
[58] Field of Search ................... 435/5, 6, 7.1; 536/23.1; 530/300, 350

[56] References Cited

PUBLICATIONS

Xiao et al., Molecular and Cellular Biology, Sep. 1990, vol. 10, No. 9: pp. 4974–4977.
Haigh et al., Nature, Mar. 15, 1990, vol. 344: pp. 257–259.

*Primary Examiner*—George C. Elliott
*Assistant Examiner*—Terry A. McKelvey
*Attorney, Agent, or Firm*—Flehr, Hohbach, Test, Albritton & Herbert

[57] ABSTRACT

Host Cell Factor (HCF), a eukaryotic cellular protein involved in transcription, nucleic acids encoding HCF, and methods of using HCF and HCF-encoding nucleic acids are provided. HCF activity is disclosed to comprise a collection of polypeptides encoded by a structural gene encoding a parent protein of 2039 amino acids. HCF-specific binding compounds are disclosed including antibodies to HCF epitopes. Because HCF is required for the transcription of a number of viral genes such as the immediate early genes of Herpes Simplex Virus, the invention provides HCF-based pharmaceutical compositions and HCF-based methods for screening chemical libraries for regulators of viral transcription. Such compositions are used in the treatment of viral infections by modulating the transcription of certain viral genes.

2 Claims, 13 Drawing Sheets

```
MASAVSPANLPAVLLQPRWKRVVGWSGPVPRPRHGHRAVAIKELIVVFGGGNEGIVDELH       60
VYNTATNQWFIPAVRGDIPPGCAAYGFVCDGTRLLVFGGMVEYGKYSNDLYELQASRWEW      120
KRLKAKTPKNGPPPCPRLGHSFSLVGNKCYLFGGLANDSEDPKNNIPRYLNDLYILELRP      180
GSGVVAWDIPITYGVLPPPRESHTAVVYTEKDNKKSKLVIYGGMSGCRLGDLWTLDIDTL      240
TWNKPSLSGVAPLPRSLHSATTIGNKMYVFGGWVPLVMDDVKVATHEKEWKCTNTLACLN      300
LDTMAWETILMDTLEDNIPRARAGHCAVAINTRLYIWSGRDGYRKAWNNQVCCKDLWYLE      360
TEKPPPPARVQLVRANTNSLEVSWGAVATADSYLLQLQKYDIPATAATATSPTPNPVPSV      420
PANPPKSPAPAAAAPAVQPLTQVGITLLPQAAPAPPTTTTIQVLPTVPGSSISVPTAART      480
QGVPAVLKVTGPQATTGTPLVTMRPASQAGKAPVTVTSLPAGVRMVVPTQSAQGTVIGSS      540
PQMSGMAALAAAAAATQKIPPSSAPTVLSVPAGTTIVKTMAVTPGTTTLPATVKVASSPV      600
MVSNPATRMLKTAAAQVGTSVSSATNTSTRPIITVHKSGTVTVAQQAQVVTTVVGGVTKT      660
ITLVKSPISVPGGSALISNLGKVMSVVQTKPVQTSAVTGQASTGPVTQIIQTKGPLPAGT      720
ILKLVTSADGKPTTIITTTQASGAGTKPTILGISSVSPSTTKPGTTTIIKTIPMSAIITQ      780
AGATGVTSSPGIKSPITIITTKVMTSGTGAPAKIITAVPKIATGHGQQGVTQVVLKGAPG      840
QPGTILRTVPMGGVRLVTPVTVSAVKPAVTTLVVKGTTGVTTLGTVTGTVSTSLAGAGGH      900
STSASLATPITTLGTIATLSSQVINPTAITVSAAQTTLTAAGGLTTPTITMQPVSQPTQV      960
TLITAPSGVEAQPVHDLPVSILASPTTEQPTATVTIADSGQGDVQPGTVTLVCSNPPCET     1020
HETGTTNTATTTVVANLGGHPQPTQVQFVCDRQEAAASLVTSTVGQQNGSVVRVCSNPPC     1080
ETHETGTTNTATTIATSNMAGDHGCSNPPCETHETGTTNTATTAMSSVGANHQRDARRACA   1140
AGTPAVIRISVATGALEAAQGSKSQCQTRQTSATSTTMTVMATGAPCSAGPLLGPSMARE    1200
PGGRSPAFVQLAPLSSKVRLSSPSIKDLPAGRHSHAVSTAAMTRSSVGAGEPRMAPVCES    1260
LQGGSPSTTVTVTALEALLCPSATVTQVCSNPPCETHETGTTNTATTSNAGSAQRVCSNP    1320
PCETHETGTTHTATTATSNGGTGQPEGGQQPPAGRPCETHQTTSTGTTMSVSVGALLPDA    1380
TSSHRTVESGLEVAAAPSVTPQAGTALLAPFPTQRVCSNPPCETHETGTTHTATTVTSNM    1440
SSNQDPPPAASDQGEVESTQGDSVNITSSSAITTTVSSTLTRAVTTVTQSTPVPGPSVPP    1500
PEELQVSPGPRQQLPPRQLLQSASTALMGESAEVLSASQTPELPAAVDLSSTGEPSSGQE    1560
SAGSAVVATVVVQPPPPTQSEVDQLSLPQELMAEAQAGTTTLMVTGLTPEELAVTAAAEA    1620
AAQAAATEEAQALAIQAVLQAAQQAVMGTGEPMDTSEAAATVTQAELGHLSAEGQEGQAT    1680
TIPIVLTQQELAALVQQQQLQEAQAQQQHHHLPTEALAPADSLNDPAIESNCLNELAGTV    1740
PSTVALLPSTATESLAPSNTFVAPQPVVVASPAKLQAAATLTEVANGIESLGVKPDLPPP    1800
PSKAPMKKENQWFDVGVIKGTNVMVTHYFLPPDDAVPSDDDLGTVPDYNQLKKQELQPGT    1860
AYKFRVAGINACGRGPFSEISAFKTCLPGFPGAPCAIKISKSPDGAHLTWEPPSVTSGKI    1920
IEYSVYLAIQSSQAGGELKSSTPAQLAFMRVYCGPSPSCLVQSSSLSNAHIDYTTKPAII    1980
FRIAARNEKGYGPATQVRWLQETSKDSSGTKPANKRPMSSPEMKSAPKKSKADGQ        2035
```

FIG. 3A

| #  | Key      | From | To   | Shown...    | Description           |
|----|----------|------|------|-------------|-----------------------|
| 1  | ACT SITE | 21   | 31   | Underline...| pep R60               |
| 2  | ACT SITE | 168  | 186  | Underline...| pep R37               |
| 3  | ACT SITE | 333  | 340  | Underline...| pep R52               |
| 4  | ACT SITE | 426  | 449  | Underline...| pep 362               |
| 5  | ACT SITE | 511  | 526  | Underline...| pep 329               |
| 6  | ACT SITE | 578  | 594  | Underline...| pep 223 first sequence|
| 7  | ACT SITE | 594  | 611  | Underline...| pep R26 first sequence|
| 8  | ACT SITE | 611  | 623  | Underline...| pep 223 second sequence|
| 9  | ACT SITE | 723  | 731  | Underline...| pep 318               |
| 10 | ACT SITE | 802  | 813  | Underline...| pep 299               |
| 11 | ACT SITE | 813  | 820  | Underline...| pep 268               |
| 12 | ACT SITE | 836  | 847  | Underline...| pep R26 second sequence|
| 13 | ACT SITE | 1010 | 1031 | Boxed/Fat...| repeat 1              |
| 14 | ACT SITE | 1072 | 1093 | Boxed/Fat...| repeat 2              |
| 15 | ACT SITE | 1101 | 1126 | Boxed/Fat...| repeat 3              |
| 16 | ACT SITE | 1158 | 1183 | Boxed/Fat...| repeat 4              |
| 17 | ACT SITE | 1286 | 1311 | Boxed/Fat...| repeat 5              |
| 18 | ACT SITE | 1314 | 1339 | Boxed/Fat...| repeat 6              |
| 19 | ACT SITE | 1349 | 1374 | Boxed/Fat...| repeat 7              |
| 20 | ACT SITE | 1414 | 1439 | Boxed/Fat...| repeat 8              |
| 21 | ACT SITE | 1774 | 1781 | Underline...| pep 293 second sequence|
| 22 | ACT SITE | 1808 | 1819 | Underline...| pep 115               |
| 23 | ACT SITE | 1819 | 1840 | Underline...| pep 261 first sequence|
| 24 | ACT SITE | 1853 | 1863 | Underline...| pep 240               |
| 25 | ACT SITE | 1901 | 1919 | Underline...| pep R32               |
| 26 | ACT SITE | 1919 | 1930 | Underline...| pep 261 second sequence|

FIG. 3B

```
1    TLVCSNPPCETHETGTTNTATTTVVA
2    VRVCSNPPCETHETGTTNTATTATSN
3    QHGCSNPPCETHETGTTNTATTAMSS
4    AAQGSKSQCQTRQTSATSTTMTVMAT
5    TQVCSNPPCETHETGTTNTATTSNAG
6    QRVCSNPPCETHETGTTHTATTATSN
7    QQPPAGRPCETHQTTSTGTTMSVSVG
8    QRVCSNPPCETHETGTTHTATTVTSN

CON  QRVCSNPPCETHETGTTNTATTATSN
```

FIG. 3C

Nucleotide Sequence of HCF cDNA Clone

```
AGGCGGCTCAAGATGGCGGCTCCCAGGGCCTCCCGCCCGAGCTTGTAAGCGGGAGCGCCC      60
GGACAAGTAGTCGGGGCGACGGGACTCAGCGGCCTCCAGCTTCTTGAGCCTAGGCGCTCG     120
ACAGTTTCGGGCGGCTCTTGCGGAGACGGGGTGAGCGAGAAGAAAGGGAAGAGCCAAAGG     180
GAAGGAGGGCAGTTAAGATGGCGGCCTCCATGGAGTCGTCTACCGCTGTGTGAGAAACCG     240
CTTCTCCGTGAGAGCTGCCTTAGACGAAAGGGGGTGTGTGAAAGGAATTGAGGGGCTCCC     300
TTCCCGCTTGTTGACTTCTCCCCACCGCACCCTTTCCCGGAACTATGGCTTCGGCCGTGT     360
CGCCCGCCAACTTGCCAGCGGTGCTTCTGCAGCCCCGCTGGAAGCGAGTGGTGGGCTGGT     420
CGGGTCCGGTGCCACGGCCCCGCCACGGCCACCGCGCCGTGGCCATCAAGGAGCTCATCG     480
TGGTGTTTGGCGGCGGCAACGAGGGAATAGTGGACGAACTGCACGTGTACAACACGGCAA     540
CCAACCAGTGGTTCATCCCAGCCGTGAGGGGGGACATTCCCCCTGGGTGTGCAGCCTATG     600
GCTTCGTGTGTGACGGGACTCGCCTCCTGGTGTTTGGTGGGATGGTGGAGTATGGGAAAT     660
ACAGCAATGACCTCTACGAACTCCAGGCGAGCCGGTGGGAGTGGAAGAGACTCAAAGCAA     720
AGACGCCCAAAAACGGGCCCCCTCCGTGTCCTCGACTCGGGCACAGCTTCTCCCTTGTGG     780
GCAACAAATGCTACCTGTTTGGGGGTCTGGCCAATGATAGCGAGGACCCAAAGAACAACA     840
TTCCAAGGTACCTGAATGACTTATATATCCTGGAATTACGGCCAGGCTCTGGAGTGGTAG     900
CCTGGGACATTCCCATCACTTACGGGGTCCTACCACCACCCCGGGAGTCACATACTGCCG     960
TGGTCTACACCGAAAAAGACAATAAGAAGTCCAAGCTGGTGATCTACGGCGGGATGAGTG    1020
GCTGCAGGCTGGGGGACCTGTGGACCCTAGATATTGACACCCTGACGTGGAATAAGCCCA    1080
GTCTCAGCGGGGTGGCGCCTCTTCCTCGCAGTCTCCACTCGGCAACCACCATCGGAAATA    1140
AAATGTACGTGTTTGGTGGCTGGGTGCCTCTCGTCATGGATGACGTCAAAGTGGCCACAC    1200
ACGAGAAGGAGTGGAAGTGTACCAACACGCTGGCTTGTCTCAACCTGGATACCATGGCCT    1260
GGGAGACCATCCTGATGGATACACTGGAGGACAACATCCCCCGTGCTCGGGCTGGCCACT    1320
GCGCAGTCGCCATCAACACCCGCCTGTACATTTGGAGTGGGCGTGACGGCTACCGCAAGG    1380
CCTGGAACAACCAGGTCTGCTGCAAGGACCTCTGGTACCTAGAGACAGAAAAGCCACCAC    1440
CCCCAGCCCGAGTACAACTGGTACGCGCCAACACCAACTCCCTGGAGGTGAGCTGGGGGG    1500
CAGTGGCAACAGCCGACAGCTACCTTCTCCAGCTCCAGAAATATGACATTCCTGCCACGG    1560
CTGCTACTGCCACCTCCCCTACACCCAATCCGGTCCCATCTGTGCCTGCCAACCCTCCCA    1620
AGAGCCCTGCCCCAGCAGCAGCCGCACCTGCTGTGCAGCCGCTGACCCAAGTAGGCATCA    1680
CGCTCCTGCCCCAGGCTGCCCCGCACCCCCGACCACCACCACCATCCAGGTCTTGCCAA    1740
CGGTGCCTGGCAGCTCCATTTCTGTGCCCACCGCAGCCAGGACTCAAGGTGTCCCTGCTG    1800
TTCTCAAAGTGACCGGTCCTCAGGCTACAACAGGAACTCCATTGGTCACCATGCGACCTG    1860
CCAGCCAGGCTGGGAAAGCCCTGTCACCGTGACCTCCCTTCCCGCCGGAGTGCGGATGG    1920
TTGTGCCAACACAGAGTGCCCAGGGAACGGTGATTGGCAGTAGCCCACAGATGAGTGGGA    1980
TGGCCGCACTGGCCGCTGCGGCCGCTGCCACCCAGAAGATCCCCCCTTCCTCGGCACCCA    2040
CGGTGCTGAGTGTCCCAGCGGGTACCACCATCGTGAAGACCATGGCTGTGACACCTGGCA    2100
CTACCACCCTCCCAGCCACTGTGAAGGTGGCCTCCTCGCCAGTCATGGTGAGCAACCCTG    2160
CCACTCGCATGCTGAAGACTGCAGCCGCCCAGGTGGGGACATCGGTTTCCTCCGCCACCA    2220
ACACGTCTACCCGCCCTATCATCACAGTGCACAAGTCAGGCACTGTGACAGTGGCCCAGC    2280
AAGCCCAGGTGGTGACCACAGTTGTGGGCGGGGTCACCAAGACCATCACCCTGGTGAAGA    2340
GCCCCATCTCTGTCCCAGGAGGCAGTGCTCTGATTTCCAATCTGGGCAAAGTGATGTCGG    2400
```

FIG. 3D-1

```
TGGTCCAGACCAAACCAGTTCAGACTTCAGCAGTCACAGGCCAGGCGTCCACGGGTCCTG    2460
TGACTCAGATCATCCAGACCAAAGGGCCCCTGCCAGCGGGAACAATCCTGAAGCTGGTGA    2520
CCTCAGCAGATGGCAAGCCCACCACCATCATCACTACCACGCAGGCAGTGGGGCGGGGA     2580
CCAAGCCCACCATCCTGGGCATCAGCAGCGTCTCCCCAGTACCACCAAGCCCGGCACGA     2640
CCACCATCATCAAAACCATCCCCATGTCGGCCATCATCACCCAGGCGGGCGCCACGGGTG    2700
TGACCAGCAGTCCTGGCATCAAGTCCCCCATCACCATCATCACCACCAAGGTGATGACTT    2760
CAGGAACTGGAGCACCTGCGAAAATCATCACTGCTGTCCCCAAAATTGCCACTGGCCACG    2820
GGCAGCAGGGAGTGACCCAGGTGGTGCTTAAGGGGGCCCCGGGACAGCCAGGCACCATCC    2880
TCCGCACTGTGCCCATGGGGGGTGTTCGCCTGGTCACACCCGTCACCGTCTCCGCCGTCA    2940
AGCCAGCCGTCACCACGTTGGTTGTGAAAGGCACCACAGGTGTCACGACCCTAGGCACAG    3000
TGACAGGCACCGTCTCCACCAGCCTTGCCGGGGCGGGGGGCCACAGCACTAGTGCTTCCC    3060
TGGCCACGCCCATCACCACCTTGGGCACCATTGCCACCCTCTCAAGCCAGGTGATCAACC    3120
CCACTGCCATCACTGTGTCGGCCGCACAGACCACGCTGACAGCGGCAGGCGGGCTCACAA    3180
CCCCAACCATCACCATGCAGCCCGTGTCCCAGCCCACCCAGGTAACTCTGATCACGGCAC    3240
CTAGTGGGGTGGAGGCCCAGCCTGTGCATGACCTCCCTGTGTCCATTCTGGCCTCCCCGA    3300
CTACAGAACAGCCCACCGCCACAGTTACCATCGCCGACTCAGGCCAGGGTGATGTGCAGC    3360
CTGGCACTGTCACCTTGGTGTGCTCCAACCCACCCTGTGAGACCCACGAGACTGGCACCA    3420
CCAACACGGCCACCACTACTGTTGTGGCTAACCTTGGGGGACACCCCCAGCCCACCCAAG    3480
TGCAGTTCGTCTGTGACAGACAGGAGGCAGCTGCTTCTCTTGTGACCTCGACTGTGGGCC    3540
AGCAGAATGGTAGCGTGGTCCGAGTCTGTTCGAACCCGCCCTGCGAGACCCACGAGACGG    3600
GCACCACCAACACCGCCACCACCGCCACCTCCAACATGGCCGGGCAGCATGGCTGCTCAA    3660
ACCCACCCTGCGAGACCCACGAGACGGGCACCACCAACACTGCCACTACAGCCATGTCGA    3720
GCGTCGGCGCCAACCACCAGCGAGATGCCCGTCGGGCCTGTGCAGCTGGCACCCCTGCCG    3780
TGATCCGGATCAGTGTGGCCACTGGGGCGCTGGAGGCAGCCCAGGGCTCTAAGTCCCAGT    3840
GCCAAACCCGCCAGACCAGCGCGACCAGCACCACCATGACTGTGATGGCCACCGGGGCCC    3900
CGTGCTCGGCCGGCCCACTCCTTGGGCCGAGCATGGCACGGGAGCCCGGGGGCCGCAGCC    3960
CTGCTTTTGTGCAGTTGGCCCCTCTGAGCAGCAAAGTCAGGCTGAGCAGCCCAAGCATTA    4020
AGGACCTTCCTGCGGGGCGCCACAGCCATGCGGTCAGCACCGCTGCCATGACCCGTTCCA    4080
GCGTGGGTGCTGGGGAGCCCGCATGGCACCTGTGTGCGAGAGCCTCCAGGGTGGCTCGC    4140
CCAGCACCACAGTGACTGTGACAGCCCTGGAGGCACTGCTGTGCCCCTCGGCCACCGTGA    4200
CCCAAGTCTGCTCCAACCCACCATGTGAGACCCACGAGACAGGCACCACCAACACCGCCA    4260
CTACCTCGAATGCAGGCAGCGCCCAGAGGGTGTGCTCCAACCCGCCATGCGAGACCCACG    4320
AGACGGGCACCACCCACACGGCCACCACCGCTACTTCAAACGGGGGCACGGGCCAGCCCG    4380
AGGGTGGGCAGCAGCCCCCTGCTGGTCGCCCCTGTGAGACACACCAGACCACTTCCACTG    4440
GCACCACCATGTCGGTCAGCGTGGGTGCCCTGCTTCCCGACGCCACTTCTTCCCACAGGA    4500
CCGTGGAGTCTGGCCTAGAGGTGGCGGCGGCACCCAGCGTCACCCCCCAGGCTGGCACCG    4560
CGCTGCTGGCTCCTTTCCCAACACAGAGGGTGTGCTCCAACCCCCCTGTGAGACCCACG    4620
AGACGGGCACCACTCACACGGCCACCACTGTCACTTCCAACATGAGTTCAAACCAAGACC    4680
CCCACCTGCTGCCAGCGATCAGGGAGAGGTGGAGAGCACCCAGGGCGACAGCGTGAACA    4740
TCACCAGCTCCAGTGCCATCACGACAACCGTGTCCTCCACACTGACGCGGGCTGTGACCA    4800
CCGTGACGCAGTCCACACCGGTCCCGGGCCCCTCTGTGCCGCCCCCAGAGGAACTCCAGG   4860
```

FIG. 3D-2

```
TGTCGCCAGGTCCTCGCCAGCAGCTGCCGCCACGGCAGCTTCTGCAGTCGGCTTCCACAG  4920
CCCTGATGGGGGAGTCCGCCGAGGTCCTGTCAGCCTCCCAGACCCCTGAGCTCCCGGCCG  4980
CCGTGGATCTGAGCAGCACAGGGGAGCCATCTTCGGGCCAGGAGTCTGCCGGCTCTGCGG  5040
TGGTGGCCACTGTGGTGGTCCAGCCACCCCCACCCACACAGTCCGAAGTAGACCAGTTAT  5100
CACTTCCCCAAGAGCTAATGGCCGAGGCCCAAGCTGGCACCACCACCCTCATGGTAACGG  5160
GGCTCACCCCCGAGGAGCTGGCAGTGACGGCTGCTGCAGAAGCAGCTGCCCAGGCCGCAG  5220
CCACGGAGGAAGCCCAGGCCCTGGCCATCCAGGCGGTGCTCCAGGCCGCGCAGCAGGCCG  5280
TCATGGGCACCGGCGAGCCCATGGACACCTCCGAGGCAGCAGCAACCGTGACTCAGGCGG  5340
AGCTGGGGCACCTGTCGGCCGAGGGTCAGGAGGGCCAGGCCACCACCATACCCATTGTGC  5400
TGACACAGCAGGAGCTGGCTGCCCTGGTGCAGCAGCAGCAGCTGCAGGAGCCCAGGCCC  5460
AGCAGCAGCATCACCACCTCCCCACTGAGGCCCTGGCCCCTGCCGACAGTCTCAACGACC  5520
CAGCCATTGAGAGCAATTGCCTCAATGAGCTGGCCGGCACGGTCCCCAGCACTGTGGCGC  5580
TGCTGCCCTCAACGGCCACTGAGAGCCTGGCTCCATCCAACACATTTGTGGCCCCCCAGC  5640
CGGTTGTGGTGGCCAGCCCAGCCAAGCTGCAGGCTGCAGCTACCCTGACCGAAGTGGCCA  5700
ATGGCATCGAGTCCCTGGGTGTGAAGCCAGACCTGCCGCCCCCACCCAGCAAAGCCCCCA  5760
TGAAGAAGGAAAACCAGTGGTTTGATGTGGGAGTCATTAAGGGCACCAATGTAATGGTGA  5820
CACACTATTTCCTGCCACCAGATGATGCTGTCCCATCAGACGATGATTTGGGCACCGTCC  5880
CTGACTATAACCAGCTGAAGAAGCAGGAGCTGCAGCCAGGCACAGCCTATAAGTTTCGTG  5940
TTGCCGGAATCAATGCCTGTGGCCGGGGCCCTTCAGCGAAATCTCAGCCTTTAAGACGT  6000
GCCTGCCTGGTTTCCCAGGGGCCCCTTGTGCCATTAAAATCAGCAAAAGTCCGGATGGTG  6060
CTCACCTCACCTGGGAGCCACCCTCTGTGACCTCCGGCAAGATTATCGAGTACTCCGTGT  6120
ACCTGGCCATCCAGAGCTCACAGGCTGGGGCGAGCTCAAGAGCTCCACCCCGGCCCAGC  6180
TGGCCTTCATGCGGGTGTACTGTGGGCCCAGCCCCTCCTGCCTGGTGCAGTCCTCCAGCC  6240
TTTCCAACGCCCACATCGACTACACCACCAAGCCCGCCATCATCTTCCGCATCGCCGCCC  6300
GCAATGAGAAGGGCTATGGCCCGGCCACACAAGTGAGGTGGCTGCAGGAAACCAGTAAAG  6360
ACAGCTCTGGCACCAAGCCAGCCAACAAGCGGCCCATGTCCTCTCCAGAAATGAAATCTG  6420
CTCCAAAGAAATCTAAGGCCGATGGTCAGTGAGAGGAAGCTGACTAGCCCCTGGATTCTT  6480
CTCCAGACCCCCTGCTTCAGGAACACCCGCCAGGGCCCACCCCTCCCACCCCGTCCCAG  6540
CATTCGCACTTCACCCTCGCGAGCCGCTGTTCACTCCTCTCCCCTTTCTCTTTCTCTCTG  6600
TTTTTAAAATAATCTAAAGAAAGCACATTTTACCATTGCTGTTGGGAGGAAGCAGAGGCA  6660
GATGGGAAAGCAGAGAGAGGAGCGCGCTTCCTTTCCTCCCCGCTGCCGCCCACCCTGGGG  6720
AGAGACTTTTGCGGGGAGGGAAGGCGGAGCTGAGGACAGCCAGCTCCGCCCTCCCAAGGC  6780
TGTGCGTTCCTGAGGGCCAGGTCGGGGGCAGGCATGGAGGGGAGGAAAGGCGTCCCTCTT  6840
GGCCCTCCCCAGAGTGGCTTTCCTGGCACCCTGGCCTGGGTGTCTGGTTCTGTTTTCTTT  6900
TCTTCCCCTTGTGTTTCCAGTCACCTAACTTCCCTTCCTCAGGCTCCCCCGGCCCACCCT  6960
GCTCAGTGACCCCACAGGAAGCTTACACATTTTCTCAGAGGCCTTTGTGCTCCCACCTCT  7020
TCTACCCTCCCCCTCTTCTTTCCCATTTTAAAAAAGAAAAGAAGGAAAAAGAAAAAAGGG  7080
GCAAGGAGCCCCGCGGCGGCCTGGGCAGCGCCTGTGCAGACCTCCCTGCAGGCCGCACTG  7140
CCAACTGCTGCATTTGTTGTGTTTTTAGGTTGCAATTGGTGAAGTTCACACTTTCATTG  7200
TAATTTTAGCGTGTGGGGTTTTGTCCCTTTTTTGTTGTTGTTAGCTGTGTACAGAATGTG  7260
TAACCTTTTTTCTTTTCTCTTTTTTTGTTTTGTTTTGTTTTGTTTTGTTTTTTACTTT    7320
```

FIG. 3D-3

```
TTTCTTCTTGGCTAATTCTTGGCAGGGATCTTTCTGGAGGAAAAGCTGGGGCCAGCCAGG 7380
GCAGGAGAGGTGTGAAATCTGCCACGAGGGGCCTGCTGTTTGCCACCCAGCCCAACTTCC 7440
TGTTGCTGGCCCCTGCCCTCTGCCCTTTTGCCTGTCCTCAGGCCGCTGGAACAAAGGAAG 7500
GACAGCTCATTCCTCATGGGCGATCACTCCGCATCTATAGGGTCGAGCCTAGGGGAGCTT 7560
GAGGGAGGGCTGGGGCCTCCTTGTCCTGGATTTCCAGCTCTCCCCATCCCCCCTCCCTGA 7620
GCACCACCGGCACCGCCTCCCAAACAGGGCTGCTGGTTTCCGCAGCCACTGCTCCACCTC 7680
CCCCAAATCGTCATGGAAAGGGTGGAGATGGAGGGGAACCAGGCGTCCTTGGAGGCAGCT 7740
TGGGAGGGTGACTGTGTAGTGTCACCCACAAGGGAGGCTAGGGCAATGGAGCAGGCCACC 7800
AGCAGCAGCTGTGCAGCATGGAACTCAGGCCAGGCTCCGAGGCTGGGGGATCTGCTTGGA 7860
GTTTTCTGCCCCCCACCCCAAACTTCTGTCGAGGAGCAAGGCTTGCCAGCAAGTCAGAAG 7920
GATTTGAACCGAGCAGCCAATCTTTCCAGCCCTCCCCTACCGACCTCTGCCTGGAGACGC 7980
AGCAGCCTGTGTCCTCCAGGGCCTCTGGTTTGTTGTATTATAGTATATTTCGCTGTGGAA 8040
AATGTCACGTTTAGTCACCTTGGAGCCCACTCACCTGGTCCTGTTGTTTTACCCCATCCC 8100
TTCTCTCGCGCGCCTATTGATTTGTTTCTGAGGAGAGTACACCGTTCÁCTATTGTAGAGT 8160
AACCCCTGTGACTCAATATTACCATAGTGCGATGTCGTTTTGTGCTATTTTGAACAATTA 8220
AAAGACTTTTTTTGAAATAAAAAAAAAAAAAAA                            8252
```

HERPES SIMPLEX VIRUS DRUG SCREEN

The research carried out in the subject application was supported in part by grants from the National Institutes of Health. The government may have rights in any patent issuing on this application.

CROSS-REFERENCE TO RELATED APPLICATIONS

This is a division of application Ser. No. 8/046,585 filed Apr. 12, 1993 now U.S. Pat. No. 5,453,362, which is a continuation-in-part of application Ser. No. 07/989,842, filed Dec. 4, 1992, now abandoned.

INTRODUCTION

1. Technical Field

The technical field of this invention concerns Host Cell Factor, HCF, a eukaryotic cellular protein involved in transcription, nucleic acids encoding HCF, and methods of using HCF and HCF encoding nucleic acids.

2. Background

Approximately half the United States population is infected with Herpes Simplex Virus type 1 (HSV-1). The usual mode of HSV-1 infection is by direct person-to-person contact in early life—usually at abrasions around the mouth and lips. The initial infection is most often asymptomatic resulting in latent viral infection of the trigeminal ganglia. HSV-1 presents clinically as recurrent orolabial lesions heralded by a prodrome of pain, burning, or itching. Lesions typically last about ten days and reoccur with a period between one and twelve months.

Herpes Simplex Virus type 2, or genital herpes, is an extremely wide spread and serious sexually transmitted disease. About a quarter of the U.S. population is infected with HSV type 2. Infection occurs primarily in adolescents and young adults, resulting in illness lasting several weeks. Multiple lesions occur on the genitalia, which in females are often excruciatingly painful.

HSV (types 1 and 2) patients compromised by either immune therapy, underlying disease, or immune suppression may suffer from more severe, disseminated lesions. There is no cure for HSV infection. Acyclovir, the only current treatment, may cause fetal abnormalities and maternal toxicity, can lead to the emergence of less sensitive or resistant virus, and does not eliminate latent HSV.

Efficacious treatment of viral diseases is the holy grail of the pharmaceutical industry. Much of this industry's current efforts are focused on identifying viral-specific drugs. Ideal treatments for viral infections are those that specifically interfere with viral function, such as viral-specific transcription. The HSV transcription factor VP16 presents an ideal target for drug targeting. Unfortunately, the complexity of VP16-mediated HSV transcription has made it impossible to assemble the components required for efficient assays for identifying potential VP16-targeted drugs.

VP16 transactivates HSV immediate early (IE) genes. The IE promoter regions contain 5'-TAATGARAT-3' elements that are frequently overlapped by octamer element related sequences to yield a sequence such as 5'-ATGCTAATGA-RAT-3' (SEQ ID NO: 01) (octamer element underlined). IE gene activation appears to require the interaction of this promoter region with a complex of VP16, Oct1 or a related protein, and a nuclear fraction, variously termed host cell factor (HCF), C1, VCAF, and CFF. Until the present disclosure, HCF has defied characterization and identification. Without a source of recombinant HCF, it is not possible to assemble a defined assay for VP16-mediated transcription. Accordingly, the present invention provides the pharmaceutical industry with the critical, missing ingredient for Herpes virus drug development.

Relevant Literature

Kristie and Sharp (1993), J Biol Chem 268, 6525–6534; Stern and Herr (1991), Genes and Development 5, 2555–2566; Xiao and Capone (1990), Molecular and Cellular Biology 10 (9), 4974–4977; Kristie and Sharp (1990), Genes and Development 4, 2382–2396; Haigh, et al. (1990), Nature 344, 257–259; Katan et at. (1990), Nucleic Acids Research 18, 6871–6880; Kristie et al. (1989) EMBO J. 8, 4229–4238; Gerster and Roeder (1988) Proc. Natl. Acad. Sci. U.S.A 85, 6347–6351; and Stern et al. (1989), Nature 341,624–630 relate to the VP16 transcription complex.

SUMMARY OF THE INVENTION

Host Cell Factor (HCF), related eukaryotic nuclear proteins involved in transcription, nucleic acids encoding HCF, and methods of using HCF and HCF-encoding nucleic acids are provided. HCF activity comprises a collection of polypeptides encoded by a single structural gene encoding a parent protein of about 2039 amino acids. HCF-specific binding compounds are disclosed including antibodies to HCF epitopes. HCF is required for the transcription of a number of viral genes, such as the immediate early Herpes simplex virus I genes. The invention provides HCF-based pharmaceutical compositions and HCF-based methods for screening chemical libraries for regulators of viral transcription. Such compositions are used in the treatment of viral infections by modulating the transcription of certain viral genes, especially those whose promoters contain the TAAT-GARAT element.

(A) Diagram depicting the purification scheme. For details see Experimental Procedures.

(B) HCF-associated polypeptides fall into three size classes. A representative HCF preparation was electrophoresed on a 7% SDS-polyacrylamide gel and visualized by silver staining. The relative mobilities and sizes (in KDa) of the molecular weight markers (lane M) are indicated.

(C) Glycerol gradient sedimentation of HCF. Aliquots (10 microliters) from each fraction were analyzed on a 6% SDS-polyacrylamide gel. Proteins were stained with silver. The sizes of the protein molecular weight markers are given on the left. An aiiquot of the load material (10 ul) is also shown on the left.

(D) Sedimentation of HCF activity. The fractions shown in panel C were tested for HCF activity by gel mobility-shift assay. An aiiquot of each fraction was diluted ten-fold in fetal calf serum (included to prevent non-specific protein loss) and 1 ul of this was assayed with GST-VP16, Oct-1 POU domain, and labeled (octa+)TAATGARAT probe. Unbound probe is shown on the left (lane a) followed by probe mixed with HeLa nuclear extract (lane b), and probe mixed with HeLa extract, Oct-1 POU domain, and GST-VP 16 (lane c). The positions of the Oct-1 POU domain complex, Hela cell Oct-1 complex (Oct-1), and VP16-induced complex (VIC) are shown on the left. The asterisks indicates a weak HCF-independent VIC complex that is stabilized by the fetal calf serum in the reaction mixture.

FIG. 3(A)–3(C), 3(D1)–3(D4) Structure of HCF. (A) The deduced amino acid sequence of the cDNA encoding HCF (SEQ ID NO: 05) Peptides corresponding to those obtained from the purified protein species are boxed. The peptide number and parent protein band from which the amino acid sequence was obtained are given below the box; parent protein nomenclature is given in FIG. 2. The deduced amino acid sequence of the H12 insert is indicated by a bar. The two guessmers used to isolate H12 are indicated above their parent peptides. The sequences were as follows: gs-1, 5'GAG AAC CAG TGG TTT GAT GTG GGC GTG ATC AAG 3' (SEQ ID NO: 02); gs-2, 5' AAG CAG GAG CTX CAG CCT GGC ACA GCC TAC AAG 3' (SEQ ID NO: 03). (B) Table indicating peptide (underlined) and repeat (boxed) sequences of figure 3A. (C) Consensus sequence of "THE TNT" repeat (SEQUENCE ID NO: 06–14). (D) Diagram of the HCF cDNA (SEQ ID NO: 06–14). The underlined positions include the start codon (nucleotide positions 345–347), the stop codon (6450–6452), and the poly A signal sequence (8216–8223).

Figure 4:
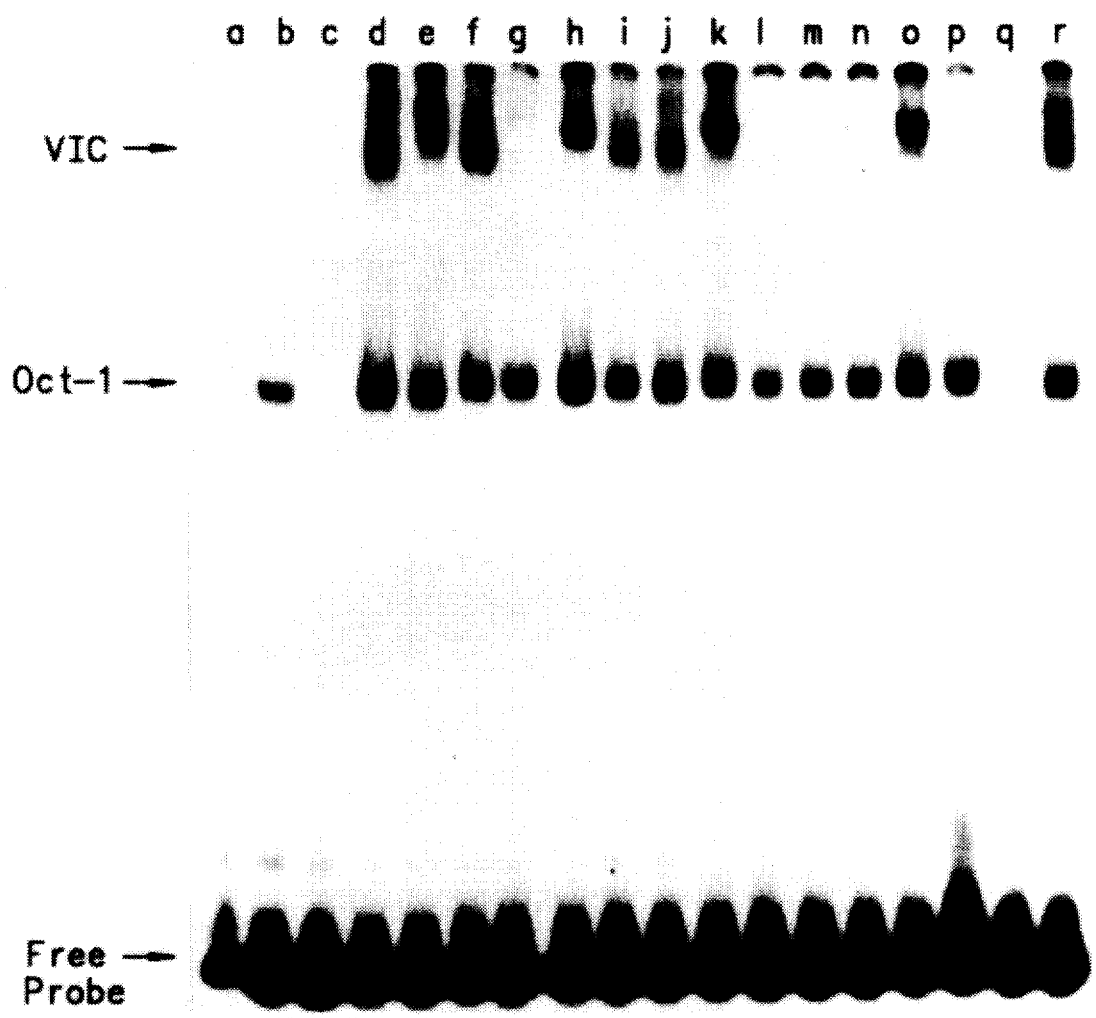

FIG. 4. Disruption of VIC by antibodies to HCF. A WGA fraction containing HCF activity was preincubated in the presence of various amounts of antisera prior to addition of the remaining EMSA reagents. a, probe alone; b, WGA fraction, no GST-VP16 DC added; c, GST-VP16DC, no WGA fraction added; d-o, and r, WGA fraction plus GST-VP16DC: e, 1:100 dilution of LP1 antibody to VP16; f, 1:10 dilution of preimmune mouse serum; g, 1:10 dilution of mouse antiserum to purified HCF; h, 1:50 dilution of mouse antiserum to purified HCF; i, 1:100 dilution of mouse antiserum to purified HCF; j, no addition; k, 1:10 dilution of preimmune rabbit serum; 1, 1:10 dilution of antiserum to rHCF; m, 1:100 dilution of rabbit antiserum to rHCF; n, 1:500 dilution of rabbit antiserum to rHCF; 0, 1:5000 dilution of rabbit antiserum to rHCF; p, WGA extract plus 1:10 dilution of rabbit antiserum to rHCF; q, GST-VP16DC plus 1:10 dilution of rabbit antiserum to rHCF; r, 1:100 dilution of control antibody 12CA5. VIC, VP16-induced complex; Oct1, Oct1—DNA complex; Free probe, $^{32}$P-labeled DNA containing the TAATGARAT element from the ICP0 gene.

Figure 5C:
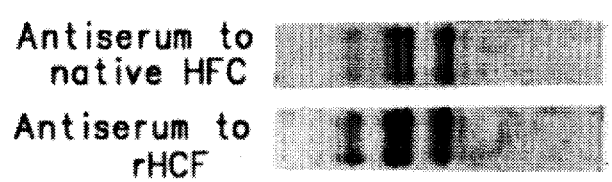
Figure 5B:
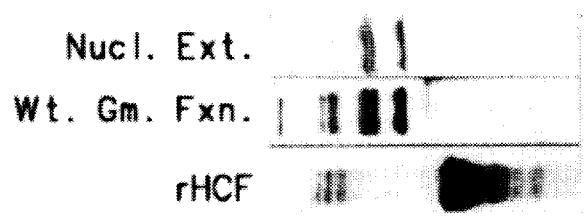
Figure 5A:
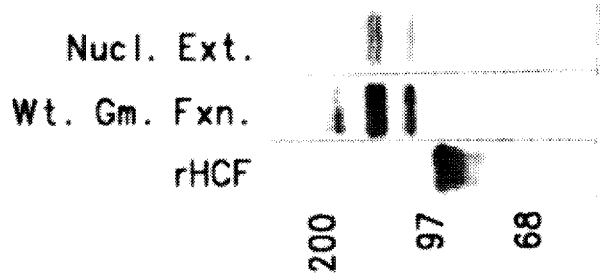

FIGS. 5(A)–5(C). Multiple forms of HCF are recognized by antiserum to recombinant HCF. Purified (FIGS. 5A, B) and whole cell (FIG. 5C) extracts were subjected to SDS PAGE, and proteins were transferred to nitrocellulose, incubated with antisera to either a purified HCF fraction (native HCF) (FIG. 5A) or recombinant HCF (FIG. 5B), and visualized by the alkaline phosphatase method (Sambrook et. al. supra). rHCF, recombinant HCF; Wt. Gm Fxn., wheat germ agglutinin fraction; Nucl. ext., nuclear extract.

Figure 6:
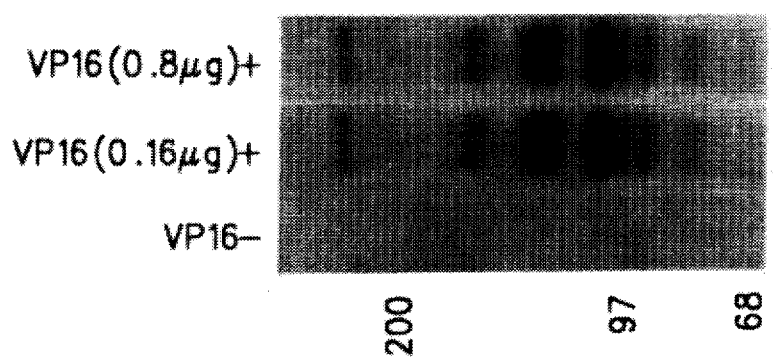

FIG. 6. HCF can be immunoprecipitated from VP16-supplemented HeLa cell extracts with an antibody to VP16. GST-VP16DC was added to freshly prepared HeLa extracts and HCF polypeptides were co-immune precipitated with the LP1 antibody. Immune complexes were subjected to SDS PAGE on a 7% acrylamide gel, transferred to nitrocellulose, and visualized with rabbit antiserum to rHCF and $^{125}$I-protein A. Additions to the extracts are indicated above each lane.

DESCRIPTION OF SPECIFIC EMBODIMENTS

Host Cell Factor (HCF), nucleic acids encoding HCF, and methods of use are provided.

As used herein, HCF refers to translation products of a nucleotide sequence substantially homologous with the disclosed HCF nucleotide sequence. HCF may be recombinant or purified from a natural source and includes xenogeneic HCF analogs. HCF translation products frequently have native post-translational modifications such as glycosylation patterns.

A polypeptide comprising an "epitope" of HCF comprises a three-dimensional structural conformation presented by a translation product of the disclosed HCF gene. Such an epitope is structurally distinguished from previously known epitopes. While an epitope is functionally defined in terms of a spatial conformation, typically epitopes are characterized by amino acid sequence homology to at least a "portion" of the disclosed HCF amino acid sequence or by antibodies, preferably monoclonal antibodies, which are capable of specifically binding a translation product of the disclosed HCF gene.

A "portion" of HCF is a peptide sequence unique to HCF in that it is not found in any previously known proteins. Thus a portion has an amino acid sequence length at least long enough to define a novel polypeptide. A portion of HCF is a polypeptide of at least about a six, preferably at least about an eighteen, more preferably at least about a thirty-six amino acid sequence of HCF and may be as long as the full length HCF of about 2039 amino acids. Portions of HCF are readily identified from the disclosed HCF amino acid sequence (SEQ ID NO: 05) by comparison to known protein sequence data bases.

"Xenogeneic" HCF analogs are nonhuman-derived proteins with substantial functional or sequence identity to HCF. Nonhuman sources of xenogeneic HCF analogs include animal sources, such as Drosophila, Spodoptera, and preferably mammalian. Of particular interest are rodents, primates, and livestock animals including bovine, ovine, equine and avian species "Functional" HCF analogs or proteins with "substantial functional identity" to HCF are compounds that exhibit one or more biochemical properties specific to HCF, such as the ability to specifically modulate the transcription of one or more TAATGARAT or octamer element containing genes; or, the capacity to facilitate VP16 association with Oct1 and TAATGARAT. Preferably, such proteins are also capable of specifically binding VP16 under conditions such as described herein.

"Substantial sequence identity" or "substantially homologous" means that a portion of the polypeptide presents at least about 70%, more preferably at least about 80%, and most preferably at least about 90% sequence identity with an HCF sequence portion. Where the sequence diverges from HCF, the differences are preferably conservative, i.e. an acidic for an acidic amino acid substitution or a nucleotide change providing a redundant codon. Dissimilar sequences are typically aggregated within regions rather than being distributed evenly over the polymer.

"Modulating transcription" means altering transcription, and includes changing the rate or level of transcription and changing the responsiveness of transcription to regulatory controls.

An "isolated" polypeptide or nucleic acid is unaccompanied by at least some of the material with which it is associated in its natural state. Generally, an isolated polypeptide constitutes at least about 1%, preferably at least about 10%, and more preferably at least about 50% by weight of the total protein in a given sample. Included in the polypeptide weight are alternative forms such as differentially glycosylated or phosphorylated or otherwise post-translationally modified forms. Stained bands of a polypeptide are readily identified by Coomassie staining when the polypeptide, in isolated form, is subjected to electrophoresis according to the method of Laemmli, U.K. (1970) Nature 227, 680–685. A composition comprising substantially pure polypeptide is at least about 10%, preferably at least about 30%, more preferably at least about 70% by weight total protein. By pure polypeptide is intended at least about 90%, preferably at least 95%, and more preferably at least about 99% by weight of protein. Protein weight percentages are determined by dividing the weight of HCF, including alternative forms of HCF and HCF analogs such as alternatively spliced, differentially phosphorylated or glycosylated, or otherwise post-translationally modified HCF, present in a fraction by the total protein weight present. Experimental methods for purifying HCF are set out below and in the following working exemplification.

An "isolated" nucleic acid sequence is present as other than a naturally occurring chromosome or transcript in its natural state and typically is removed from at least some of the nucleotide sequences with which it is normally associated with on a natural chromosome. A sequence substantially identical or homologous to an HCF epitope-encoding sequence hybridizes to a complementary HCF epitope-encoding sequence under low stringency conditions, for example, at 50° C. and SSC (0.9M saline/0.09M sodium citrate) and that remains bound when subject to washing at 55° C. with SSC. A partially pure nucleotide sequence constitutes at least about 5%, preferably at least about 30%, and more preferably at least about 90% by weight of total nucleic acid present in a given fraction. The nucleic acids of the invention and portions thereof, other than those used as PCR primers, are usually at least about 60 bp and usually less than about 6 kb in length. PCR primers are generally between about 15 and 100 nucleotides in length.

Of particular interest are portions of HCF that facilitate HCF functional or structural interaction with transcription associated factors, particularly TAATGARAT or octamer element associated transcription factors, more particularly, Oct1. Of special interest are portions of HCF that interact with VP16, and with a combination of Oct1, VP16 and DNA, and subcombinations thereof. For example, HCF can specifically bind VP16 even in the absence of DNA and Oct1. The identification of such portions is disclosed below.

Specific binding is empirically determined by contacting, for example HCF, with a mixture of components and identifying those components that preferentially bind HCF. For instance, in the case of DNA, DNA binding, specificity may be shown by competitive binding of specific (substantially complementary)- over nonspecific-oligonucleotides. Specific binding is most conveniently shown by gel shift assays with competitor DNA or by immobilizing, for example HCF, on a solid matrix such as a polymer bead or microtiter plate and contacting the immobilized HCF with a mixture. Often, one or more components of the mixture will be labelled. Another useful approach is to displace labelled ligand, like VP16, from an immobilized target, like HCF. Alternatively, the immobilized component can be VP16 and the soluble component HCF. Generally, specific binding of HCF will have binding affinity of $10^{-6}$M, preferably $10^{-8}$M, more preferably $10^{-10}$M, in the presence of Oct1, TAATGARAT and VP16 at 30° C.

Epitopes of HCF find use in defining functional domains of HCF, identifying compounds that associate with HCF, designing compounds capable of modifying transcription, for example, by binding or modulating an epitope of HCF or exploiting structural features of HCF to directly modify gene expression, and the like. In an analogous situation, a VP16-derived peptide has been reported to inhibit in vitro formation of the HSV transcription complex, Haigh et at. (1990) supra. Accordingly, peptides encoding HCF epitopes are provided that are capable of interfering with HSV transcription complex formation or modulating functional domains of HCF. Typically, such peptides are effective by competitively inhibiting an HCF domain's association with another compound, typically a protein or DNA. Preferred HCF-derived peptides are capable of interfering with the transcription of TAATGARAT or octamer element containing genes; more preferably, with HCF-VP16 association.

For example, the amino acid sequence approximately bounded by Glu22 and Glu245 comprises a highly negatively charged region. Peptides from this region find particular use as immunogens and as modulators of HCF-protein interactions. Additionally, the sequence approximately bounded by Lys286 and Lys345 comprises a highly positively charged region. Peptides from this region find particular use as immunogens and modulators of HCF-protein and HCF-nucleic acid interactions. Of particular interest are peptides approximately bounded by Glu73 and Glu121.

Associational domains of HCF are ascertainable by those skilled in the art using the methods and compositions disclosed herein. For example, HCF routants, including deletion routants can be generated from the disclosed HCF sequence and used to identify regions important for specific protein or nucleic acid interactions. Alternatively, the ability of HCF deletion mutants to support in vitro transcription or in vivo transcription in transfection assays is determined.

The invention provides recombinantly produced HCF, HCF analogs and portions thereof. These recombinant products are also readily modified through physical, chemical, and molecular techniques disclosed or cited herein or otherwise known to those skilled in the relevant art. A preferred baculovirus expression system permits the recombinant HCF to be modified, processed and transported within a eukaryotic system. According to a particular embodiment of the invention, portions of the HCF encoding sequence are spliced, using recombinant DNA technology, with heterologous sequences to produce fusion proteins. Such fusion proteins find particular use in modulating gene transcription.

For example, domains of HCF can be fused to a well-characterized DNA binding domain (see, e.g., Sadowski et at., (1988) Nature 335,563–564) and the resulting fusion protein can be tested for its ability to activate transcription. In this way, HCF transcription activation domains are identified. Alternatively, an HCF domain can be fused with a domain having endonuclease activity for site-specific DNA cleaving. Other useful HCF fusion partners include GST, Lemer epitope, an epitope recognized by a monoclonal antibody (e.g. hemagglutinin epitope and 12CA5 monoclonal antibody), glutathione S-transferase for immobilization, the VP16 activation domain, etc.

The invention also provides for functional and structural analogs of HCF. Using biochemical and molecular methods either known in the art or disclosed herein, the disclosed HCF and nucleotide sequences are used to generate nonnatural analogs of HCF. Such analogs find use as HCF antagonists, reagents for use in drug screening assays, particularly drugs effective for HSV infection, reagents for modulating transcription of TAATGARAT or octamer element containing genes, etc.

For example, the disclosed HCF sequence contains numerous serine residues which are useful sites for phosphorylafion or dephosphorylation. See e.g. methods disclosed in Roberts et at. (1991) Science 253, 1022–1026 and in Wegner et at. (1992) Science 256, 370–373.

The disclosed sequences are also used to identify and isolate natural HCF analogs. Such analogs include natural human analogs as well as xenogeneic analogs (non-human HCF). For example, an HCF activity has been identified in non-human cells, specifically, Drosophila cells.

Further, many transcription factors belong to families, for example, the Oct family includes Oct1, Oct2 and Oct3/4 and C/EBP has $C/EPBP_{\alpha\beta and \ \gamma}$—the members of which are expressed differentially, for example at different developmental periods or tissue specifically. Accordingly, the disclosed compositions and methods are used to identify, characterize, isolate, and purify such HCF-related proteins. For example, oligonuclcotides encoding functional domains of HCF are $^{32}$P-labeled and used to screen λcDNA libraries at low stringency to identify similar cDNAs that encode proteins with related functional domains. Additionally, HCF related proteins are isolated by antibody cross reactivity and PCR amplification with degenerate oligonuclcotide probes using the sequences disclosed herein.

HCF can be further modified by methods known in the art. For example, HCF is phosphorylated or dephosphorylated, glycosylated or deglycosylated, with or without radioactive labeling, etc. Phosphorylation may be involved in modulating the transcription activation activity of CREB proteins, $C/EBP_\alpha$, VP16, Oct1, Oct2, etc. Especially useful are modifications that alter HCF solubility, membrane transportability, stability, and binding specificity and affinity. Some examples include fatty acidacylation, proteolysis, and mutations in VP16 interaction domains that stabilize binding.

HCF may also be modified with a label capable of providing a detectable signal, for example, at a heart muscle kinase labeling site, either directly or indirectly. Exemplary labels include radioisotopes, fluorescers, etc. Such labeled HCF and analogs thereof find use, for example, as probes in expression screening assays for proteins that interact with HCF, or, for example, HCF binding to VP16 in drug screening assays.

Specific polyclonal or monoclonal antibodies that can distinguish HCF from other nuclear proteins are conveniently made using the methods and compositions disclosed in Harlow and Lane, Antibodies, A Laboratory Manual, Cold Spring Harbor Laboratory, 1988, other references cited herein, as well as immunological and hybridoma technologies known to those in the art. Where HCF derived peptides are used to induce an HCF-specific immune response, the peptides may be conveniently coupled to an suitable carrier such as KLH and administered in a suitable adjuvant such as Freunds. In particular, selected peptides were coupled to a lysine core carrier substantially according to the methods of Tam (1988) Proc Natl Acad Sci USA 85, 5409–5413.

Also provided are other compounds that specifically bind HCF and are obtained using immunologic, chromatographic or synthetic methods available to those skilled in the art. For example, using the procedure of PCT applications WO 84/03564, WO 84/03506, WO 86/00991, specifically binding oligopeptides may be prepared synthetically. Of particular interest are HCF-specific antibodies that can be modified to a monovalent form, such as Fab, Fab', or Fv. Anti-idiotypic antibody, especially internal imaging anti-ids are also prepared using the disclosures herein.

Anti-HCF antibodies find use, for example, in blocking HCF involvement in transcription complexes. In addition, these antibodies can be used to identify, isolate, and purify structural analogs of HCF. Anti-HCF antibodies also find use for subcellular localization of HCF under various conditions such as HSV infection, during various cell cycle phases, induction with cytokines, protein kinases such as C and A, etc. Other exemplary applications include using HCF-specific antibodies (including monoclonal or HCF-derived peptide antibodies) to immuno-deplete in vitro transcription extracts and using immuno-affinity chromatography to purify HCF, including analogs, or other nuclear factors which interact with HCF.

A wide variety of protocols are available for performing immunoassays, sequencing nucleic acid and peptide sequences, and any or all of these may be employed, depending upon the particular situation. Immunoassays include ELISA, EMIT, CEDIA, SLIFA, and the like. A number of diagnostic procedures have been described in variety of issued patents such as U.S. Pat. Nos. 3,791,932; 3,817,837; 3,998,943, and references cited therein.

The present invention discloses the purification of HCF by wheat germ agglutinin affinity chromatography. Accordingly, the invention provides glycosylated HCF, particularly, HCF containing at least an N-acetylglucosamine moiety, and for modifications to HCF glycosylation. For example, glycosidases and lectins are used to modify, including labelling, or purify HCF with particular glycosidation patterns. Such modifications can effect changes in HCF localization, stability, binding specificity, etc.

Compositions are also provided for therapeutic intervention in disease, for example, by modifying HCF or HCF encoding nucleic acids. Oligopeptides can be synthesized in pure form and can find many uses in diagnosis and therapy. These oligopeptides can be used, for example, to modulate native HCF interaction with native transcription factors or DNA. The oligopeptides will generally be more than six and fewer than about 60 amino acids, more usually fewer than about 30 amino acids, although large oligopeptides may be employed. If desired, the entire HCF molecule may be employed, but it will be frequently convenient to use a portion thereof. HCF or a portion thereof may be used in purified form, generally greater than about 90%, usually greater than about 95% pure. Methods for purifying such peptides to such purities include various forms of chromatographic, chemical, and electrophoretic separations disclosed herein or otherwise known to those skilled in the art.

HCF ENCODING NUCLEIC ACID

The invention provides nucleic acid sequences encoding an HCF epitope, including sequences substantially identical or homologous to sequences encoding an HCF epitope. Included are DNA and RNA sequences, sense and antisense. The nucleotide (cDNA) sequence encoding full length HCF (SEQ ID NO: 15) is disclosed in FIG. 3. The disclosure also provides for the disclosed HCF encoding sequence modified by transitions, transversions, deletions, insertions, or other modifications such as alternative splicing. The invention also provides for genomic HCF sequences, HCF gene flanking sequences, including HCF regulatory sequences.

For modified HCF-encoding sequences or related sequences encoding proteins with HCF-like functions, there will generally be substantial sequence identity between at least a portion thereof and a portion of HCF, preferably at least about 40%, more preferably at least 80%, most preferably at least 90%, particularly conservative substitutions, particularly within regulatory regions and regions encoding protein domains involved in protein-protein interactions, particularly HCF-VP16 interactions.

Typically, the invention's HCF encoding polynucleotides are associated with heterologous sequences. Examples of such heterologous sequences include regulatory sequences such as promoters, enhancers, response elements, signal sequences, polyadenylation sequences, etc., introns, 5' and 3' noncoding regions, etc. Other useful heterologous sequences are known to those skilled in the art or otherwise disclosed references cited herein.

Sequences encoding xenogeneic HCF are also provided. For example, HCF specific or related sequences within a genome of a nonhuman species are localized using Southern hybridization techniques. Also, the HCF encoding nucleic acids can be subject to alternative purification, synthesis, modification or use by methods disclosed in standard manuals such as Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y., 1992) or that are otherwise known in the art.

For example, the nucleic acids can be modified to alter stability, solubility, binding affinity and specificity, etc. For example, HCF encoding sequences can be selectively methylated, etc. The nucleic acid sequences of the present invention may also be modified with a label capable of providing a detectable signal, either directly or indirectly. Exemplary labels include radioisotopes, fluorescers, biotinylation, etc.

Additionally, cDNA encoding at least a portion of HCF is useful for characterizing tissue specific expression of HCF as well as changes of HCF expression over time, particularly during organismal development or cellular differentiation. Further, using expression screening in yeast as described in Current Protocols in Molecular Biology (supra), nucleic acids encoding at least a portion of HCF are used to identify nuclear factors which interact with HCF. In this example, a yeast cDNA library containing fusion genes of cDNA joined with DNA encoding the activation domain of a transcription factor (e.g. Gal4) are transfected with fusion genes encoding a portion of HCF and the DNA binding domain of a transcription factor. Clones encoding HCF binding proteins provide for the complementation of the transcription factor and are identified through transcription of a reporter gene. See, e.g. Fields and Song (1989) Nature 340, 245–246 and Chien et at. (1991) Proc Natl Acad Sci USA 88, 9578–9582.

The invention also provides vectors comprising nucleic acids encoding HCF or HCF analogs. A large number of vectors, including plasmid and vital vectors, have been described for expression in a variety of eukaryotic and prokaryotic hosts. Advantageously, vectors may also include a promotor operably linked to the HCF encoding portion. The encoded HCF may be expressed by using any suitable vectors and host cells, using methods disclosed or cited herein or otherwise known to those skilled in the relevant art. The particular choice of vector/host is not critical to the invention.

Vectors will often include one or more replication systems for cloning or expression, one or more markers for selection in the host, e.g. antibiotic resistance, and one or more expression cassettes. The inserted HCF coding sequences may be synthesized, isolated from natural sources, prepared as hybrids, etc. Ligation of the coding sequences to the transcriptional regulatory sequences may be achieved by known methods. Suitable host cells may be transformed/transfected/infected by any suitable method including electropotation, $CaCl_2$ mediated DNA uptake, viral infection, microinjection, microprojectile, or other established methods.

Appropriate host cells include bacteria, archebacteria, fungi, especially yeast, and plant and animal cells, especially mammalian cells. Of particular interest are *E. coli, B. subtilis, Saccharomyces cerevisiae,* SF9 cells, C129 cells, 293 cells, Neurospora, and CHO, COS, HeLa cells and immortalized mammalian myeloid and lymphoid cell lines. Preferred replication systems include M13, ColE1, SV40, baculovirus, lambda, adenovirus, AAV, BPV, etc. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced HCF or HCF analogs.

Nucleic acids encoding HCF may also be introduced into cells by recombination events. For example, such a sequence can be microinjected into a cell, and thereby effect homologous recombination at the site of an endogenous gene encoding HCF, an analog or pseudogene thereof, or a sequence with substantial identity to an HCF-encoding gene. Other recombination-based methods such as nonhomologous recombinations, deletion of endogenous gene by homologous recombination, especially in pluripotent cells, etc., provide additional applications.

Experimental methods for cloning HCF, sequencing DNA encoding HCF, and expressing recombinant HCF are also set out in the working exemplification below. Other useful cloning, expression, and genetic manipulation techniques for practicing the inventions disclosed herein are known to those skilled in the art.

The compositions and methods disclosed herein may be used to effect gene therapy. See, e.g. Gutierrez et at. (1992) Lancet 339,715–721. For example, cells are transfected with HCF sequences operably linked to gene regulatory sequences capable of effecting altered HCF expression or regulation. To modulate HCF translation, cells may be transfected with HCF complementary antisense polynucleotides.

One embodiment of antisense modulation employs HCF antisense sequences operably linked to gene regulatory sequences. Cells are transfected with a vector comprising an HCF sequence with a promoter sequence oriented such that transcription of the gene yields an antisense transcript capable of binding to HCF encoding mRNA. The HCF sequence of the vector is generally at least about 20 nucleotides, preferably at least about 50 nucleotides, more preferably at least about 200 nucleotides in length. Transcription of the "antisense gene" may be constitutive or inducible and the vector may provide for stable extrachromosomal maintenance or integration.

Alternatively, single-stranded antisense nucleic acid sequences, particularly DNA or deoxynucleotide analogs, that bind to genomic DNA or mRNA encoding at least a portion of HCF may be administered to the target cell at a concentration that results in a substantial reduction in HCF expression. In this embodiment, the antisense sequence is generally less than about 200 nucleotides, preferably less than about 50 nucleotides, more preferably less than about 20 nucleotides or longer in length. Alternatively, the sequence may be present as a ribozyme. The antisense sequences (including ribozymes) may be comprised of naturally occuring nucleotides, synthetic nucleotides, or combinations thereof. For example, the oxygen of the phosphate group may be replaced with sulfur, methyl, or the like.

For gene therapy involving the transfusion of HCF transfected cells, administration will depend on a number of variables that are ascertained empirically. For example, the number of cells will vary depending on the stability of the transfused cells. Transfusions media is typically a buffered saline solution or other pharmacologically acceptable solution. Similarly the amount of other administered compositions, e.g. transfected nucleic acid, protein, etc., will depend on the manner of administration, purpose of the therapy, and the like.

DRUG SCREENING AND AGENTS

The invention provides methods and compositions for identifying agents useful in modulating gene transcription, particularly genes containing the octamer element or the TAATGARAT motif. Such agents find use in the diagnosis or treatment of disease, particularly HSV infection.

Typically, prospective agents are screened from large libraries of synthetic or natural compounds. For example, numerous means are available for random and directed synthesis of saccharide, peptide, and nucleic acid based compounds. Alternatively, libraries of natural compounds in the form of bacterial, fungal, plant and animal extracts are available or readily producible. Additionally, natural and synthetically produced libraries and compounds are readily modified through conventional chemical, physical, and biochemical means. Examples of such modifications are disclosed herein.

Useful agents are identified with a range of assays employing HCF or HCF encoding nucleic acids. As examples, protein binding assays, nucleic acid binding assays and gel shift assays are useful approaches. More particularly, HCF is used in in vitro binding assays with either VP16 alone or with a combination or subcombination of VP16, Oct1 and TAATGARAT. HCF encoding nucleic acids are generally used in secondary assays, i.e. cell-based assays where HCF cDNA is introduced into cells with VP16, Oct1 and a reporter gene. The effect of prospective agents on VP16-HCF-dependent transcription is thereby determined.

Many appropriate assays are amenable to sealed-up, high throughput usage suitable for volume drug screening. Such screening will typically require the screening of at least about 10, preferably at least about 100, and more preferably at least about 1000 agents per week. Exemplary assays include assaying labeled VP16 binding to immobilized HCF, labeled HCF or HCF peptide binding immobilized VP16, etc.

A particular exemplary assay uses recombinant VP16 labelled with $^{32}$P by a heart muscle kinase. The TAATGA-RAT oligonucleotide is bound to a 96-well microtiter plate; a mixture of $^{32}$P-VP16, recombinant Oct1 and partially purified HCF is added; and the amount of $^{32}$P bound to the plate is then determined. In the presence of HCF the binding of $^{32}$P-VP16 is higher than background. The ratios of components are equivalent to those used in the gel shift assays described below. Agents disrupting HCF-VP16 binding are thereby detected.

Where the above described assays are not preferred, for example where a particular interface such as Oct1-VP16 or VP16-DNA is targeted, other useful assays are employed. For instance, an agent may interfere with the function of HCF but not with VP16-induced complex assembly (e.g. an antibody that binds to HCF but does not disrupt complex assembly would supershift the gel retardation complex and thus be detectable without disrupting the complex.) Other exemplary assays include HCF binding assays such as affinity chromatography, and gel retardation assays such as EMSA. Other examples of high throughput assays are disclosed herein or otherwise available through modifications of known methods using the disclosures herein.

Useful agents are typically those that bind to or disrupt the association of transcription associated factors. Preferred agents include those capable of modulating the expression of genes containing TAATGARAT or the octamer element, particularly those that disrupt HCF-VP16 binding. Useful agents may be found within numerous chemical classes, though typically they are organic compounds; preferably small organic compounds. Small organic compounds have a molecular weight of more than 50 yet less than about 2,500, preferably less than about 750, more preferably, less than about 250. Exemplary classes include peptides, saccharides, steroids, and the like.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxyl terminus, e.g., for the amino group, acylation or alkylation, and for the carboxyl group, esterification or amidification, or the like. Other methods of stabilization may include encapsulation, for example, in liposomes, etc.

Agents may be prepared in a variety of ways known to those skilled in the art. For example, peptides under about 60 amino acids can be readily synthesized today using conventional commercially available automatic synthesizers. Alternatively, DNA sequences may be prepared encoding the desired peptide and inserted into an appropriate expression vector for expression in a prokaryotic or eukaryotic host. A wide variety of expression vectors are available today and may be used in conventional ways for transformation of a competent host for expression and isolation. If desired, the open reading frame encoding the desired peptide may be joined to a signal sequence for secretion, so as to permit isolation from the culture medium. Methods for preparing the desired sequence, inserting the sequence into an expression vector, transforming a competent host, and growing the host in culture for production of the product may be found in U.S. Pat. Nos. 4,710,473, 4,711,843 and 4,713,339.

For therapeutic uses, the compositions and agents disclosed herein may be administered by any convenient way, preferably parenterally, conveniently in a physiologically acceptable carrier, e.g., phosphate buffered saline, saline, deionized water, or the like. Typically, the compositions are added to a retained physiological fluid such as blood or synovial fluid. Generally, the amount administered will be empirically determined, typically in the range of about 10 to 1000 µg/kg of the recipient. For peptide agents, the concentration of will generally be in the range of about 100 to 500 µg/ml in the dose administered. Other additives may be included, such as stabilizers, bactericides, etc. These additives will be present in conventional amounts. The following examples are offered by way of illustration and not by way of limitation.

EXAMPLES

EXPERIMENTAL PROCEDURES

Expression of GST-VP16 αAC and Oct1 POU domain in *Esherichia coli*. VP16 (residues 5 to 411) lacking the carboxyl-terminal acidic activation domain was expressed as a glutathione-S-transferase (GST) fusion protein from the plasmid pETGSTVP16 αAC, which was constructed as follows: the VP16-coding sequence was excised from the plasmid pRIT2T.VP16αAC wild type (Stem and Herr, 1991) as a 1.6-kb Sal I fragment and inserted into the Sal I site of a modified pUC119 polylinker (pBam/STOP) in which sequences between the Sal I and Hind III sites were changed so that the Xba I site of the polylinker is in frame to VP16 sequences beginning at the Sal I site and places an in-frame termination codon followed by a Bam HI site downstream of the coding region. The VP16 sequences were transferred as an Xba I to Bam HI fragment to a modified version of pET11c.G.POU-1 (Aurora and Herr, 1991) in which a second Xba I site in the T7 promoter leader sequence had been destroyed.

Human Oct1 POU domain was also expressed as a GST-fusion protein from the plasmid pET11c.G.POU-1 (Aurora and Herr, 1991).

GST-VP16αAC and GST-Oct1 POU fusion proteins were expressed in *E. coli* BL21 (DE3) cells and purified with glutathione-agarose essentially as described (Lai et al., 1992). The Oct1 POU domain was separated from the GST moiety by thrombin cleavage and purified to 90% homogeneity by hydroxylapatite chromatography.

HCF assay conditions.

HCF activity was measured by an electrophoretic mobility shift assay (EMSA). A 10-ml reaction contained 10 mM Tris-HCl (pH 7.9), 50 mM KCl, 1 mM dithiothreitol (DTT), 1 mM EDTA, 0.1% NP40, 1% glycerol, 2% Ficoil-400, calf thymus DNA (6.7 ng), poly d(IC) (1 mg), fetal bovine serum (FBS) (0.67 ml), recombinant Oct1 POU domain (1 ng), recombinant GST-VP16 (40 ng), protein fraction containing HCF activity (0.1–1 ml), and a $^{32}$P-end-labeled DNA fragment (20,000 cpm) that contained the IE regulatory element from the (SEQ ID NO: 04) HSV ICP0 gene [(ATGC TAAT)GATAT; termed (Octa$^+$)TAAT6ARAT]. After incubation at 30° C. for 30 min 1 ml of 30% glycerol was added, and samples were loaded onto a 4% acrylamide gel (3.9% acrylamide: 0.1% bis) in Tris pH 8.3 (200 mM ), glycine (0.2M), and EDTA (1 mM). Glycerol (30%) plus bromophenol blue and xylene cyanol was added to the side lanes of the gel, and electrophoresis was continued until the bromophenol blue had migrated at least three-quarters of the distance down the gel. The gel was then dried for 45 min and subjected to autoradiography on Kodak XAR film at 4° C. with an intensifying screen (see FIG. 1).

Purification of HCF.

HeLa S3 cells were grown in spinner flasks in Dulbecco's modified minimal essential medium (DMEM) supplemented with 5% FBS and harvested at a density of $10^6$/ml by centrifugation at 2500 rpm in a "Sorvall" H-6000A rotor for 15 min at 4° C. The cell pellet was washed with phosphate buffered saline (PBS), repelleted, snap-frozen in liquid nitrogen, and stored at −70° C. Extracts prepared from cells stored in this manner differed little in amount of HCF activity from extracts prepared from fresh cells.

All of the extract preparation and purification procedures were performed at 0° to 4° C. Buffers containing N-(2-hydroxyethyl)piperazine-N'(2-ethanesulfonic acid) (HEPES) were prepared from a 1M stock that was adjusted to pH7.9 at 4° C. with KOH. Dithiothreitol (DTT) was added fresh from a 1M stock and phenylmethylsulfonyl fluoride (PMSF) was added fresh from a 50 mg/ml stock in ethanol. Sodium metabisulfite was prepared as a fresh 1M stock in water 1 to 2 h before use. Benzamidine, sodium vanadate, and sodium fluoride were added fresh from 1.0M, 0.2 M, and 50 mM stocks, respectively.

Frozen HeLa cell pellets were thawed rapidly in cold water and nuclear extracts prepared essentially as described (Dignam et al. (1983) Nucl Acids Res 11, 1475–1489). After dounce homogenization and centrifugation (30 min; 15,000 rpm, SS34 rotor), the supernatants were immediately incubated with wheat germ agglutinin—"SEPHAROSE" (WGA) (Vector Labs, Burlingame) (5 ml of resin for every 12 l of cells) (Jackson and Tjian (1988) PNAS 86, 1781–1785) with rocking at 4° C for 1 h. The resin had been equilibrated with buffer C 20 mM HEPES pH7.9, 25% glycerol, 1.5 mM MgCl$_2$, 0.1 mM EDTA, 0.15 mg/ml DTT, 0.1% NP40, 0.2 mg/ml sodium metabisulfite, and 0.5 mM PMSF plus 0.42M NaCl. The protein-bound resin was then poured into a column, and protein was eluted with buffer C that contained 0.3M N-acetyl glucosamine (GlcNAc) and 50 mM NaCl. Fractions that contained protein as assessed by the Coomassie dye binding method (BioRad) were pooled and tested for HCF activity in an EMSA. Fractions containing HCF activity was pooled, and one of two purification schemes was carried out.

In one purification protocol, the WGA fractions that contained HCF activity were diluted with buffer C to 30 mM KCl and applied to an 8-ml "MONO S" FPLC column (Pharmacia). Protein was eluted with a 30 to 400 mM KCl gradient. Fractions were tested for HCF activity, which eluted at 150 mM. The HCF containing fractions were dialyzed against buffer C containing 50 mM KCl and loaded onto a 1-ml "MONO Q" FPLC column (Pharmacia). Protein was eluted with a 50 to 500 mM KCl gradient. Fractions that eluted between 200 and 500 mM KCl contained HCF activity.

In another purification protocol, the WGA fractions that contained HCF activity were pooled and loaded onto a 2-ml double-stranded DNA cellulose column (Sigma) pre-equilibrated in Buffer D supplemented with 0.05M KCl and developed with a 0.05M to 0.5M linear KCl gradient in buffer D. Fractions were assayed by EMSA with or without VP16 to monitor both HCF and endogenous Oct1 activities. There was a small overlap in the elution points of these activities, and these fractions were excluded from further purification.

HCF-containing fractions were pooled, adjusted to 0.1M KCl, mixed with GST-VP16αC beads, and rotated end-over-end for 30 min at 4° C. All manipulations were performed in the absence of DTT. The GST-VP16αC fusion protein was synthesized in *E. coli* as described above. Approximately 0.5 mg of GST-VP16DC were bound per ml of swollen glutathione-agarose beads. The bead slurry was poured into a "ECONOPAC" column and washed with buffer D supplemented with 0.1M KCl. The column was then washed with 5 column volumes of buffer D containing 0.3M KCl, which was followed by a wash with 5 column volumes of buffer D containing 1.0M KCl.

The 0.3M fractions were dialyzed against 10 mM Hepes-KOH pH7.6, 0.05M KCl, 10% glycerol, 1 mM DTT, 0.5 mM PMSF and concentrated on a 1-ml "MONO Q" column equilibrated in the same buffer. The column was washed with load buffer and eluted with a linear 0.05 to 0.5M KCl gradient. Activity eluted at approximately 150 mM KCl. The fractions with peak activity were pooled and gently layered (200 to 250 ml per gradient) onto a 2-ml 15 to 35% glycerol gradient prepared in 10 mM HepesKOH pH7.9, 0.1M KCl, 0.1% NP40, 1 mM DTT, 0.5 mM PMSF. The gradients were centrifuged at 4° C. for 18 h at 39,000 rpm in a SW55 Ti (Beckman) rotor. Fractions (approximately 200 ml) were collected as drops from the bottom of the gradient. Molecular weight markers of known sedimentation coefficients (Boehringer Mannheim) were applied to a parallel gradient and assayed by SDS polyacrylamide (12%) gel electrophoresis (SDS PAGE) and Coomassie Blue staining.

Preparation of whole cell extracts.

Spodoptera frugiperda Sf9 cells were obtained from B. Stillman and maintained in semi-suspension at 27° C. in TNM-FH medium (Gibco) plus 10% FBS. Drosophila Schneider line 2 (SL2) cells were grown in spinner culture (250 ml) in M3 media (Gibco) supplemented with 10% heat-denatured FBS. Cells were collected by centrifugation, washed in PBS and lysed in buffer D with 0.42M KCl and 0.5% NP40 at 4° C. Lysates were rotated for 30 min and the nuclei and cellular debris removed by centrifugation at 10,000×g. Extracts were snap frozen in liquid nitrogen and stored at −70° C.

Generation and sequencing of HCF peptides.

"MONO Q"-purified HCF fractions and glycerol gradient fractions containing about 500 ug of total protein were precipitated with one-fourth volume of 100% trichloroacetic acid (TCA) plus 4 mg/ml sodium deoxycholate. Protein pellets were acetone washed, resuspended in SDS sample buffer containing saturating amounts of urea, heated at 65° C. for 5 min, and subjected to SDS PAGE on a 7% acrylamide gel. A sample (15-ml) of the protein fraction was taken prior to TCA precipitation and subjected in parallel to SDS polyacrylamide gel electrophoresis, and this lane of the gel was subsequently silver-stained. The polypeptides on the rest of the gel were electrophoretically transfered in 192 mM glycine, 25 mM Tris base, and 0.01% SDS to a pelyvinylidene difluoride (PVDF) membrane, and the membrane was stained with 0.1% Ponceau S in 0.1% acetic acid to visualize the transfered proteins. Protein bands were excised as indicated (FIG. 2) and treated with either trypsin or endoproteinase Lys-C exactly as described in Fernandez et. al. (1992) Analytical Biochem 201, 255–264. The resulting peptides were separated by chromatography on an Applied Biosystems (ABI) RP-300 C8 column (1×250 mm, 300 A) with an ABI 130 HPLC. Chromatographic conditions were as follows: solvent A=0.1% trifluoroacetic acid (TFA), B=0.085% TFA, 90% acetonitrile; gradient=2 to 60% B over 60 min, with a flow rate of 75 ml/min. Peptide elution was monitored by absorbance at 216 nm, and peak protein fractions were collected manually and immediately frozen on dry ice. Identical elution profiles were obtained for peptides generated from the 150-kD, 120-kD, and 110-kD proteins. Peptide fractions were subjected to sequence analysis on an ABI 477A with a 120A analyzer. The conditions used were the ABI FAST-1 reaction and conversion cycles, and FAST gradient on the analyzer.

Screening of lgt10 libraries for cDNAs encoding HCF.

Oligonucleotide guessmer probes were designed on the basis of peptide sequences obtained from purified HCF as described above and are indicated in FIG. 3. The guessmer probes were end-labeled with g-$^{32}$P-ATP and T4 polynucleotide kinase and used to screen two lgt10 cDNA libraries, one from human hepatoma cells and one from human platelets. Bacteriophage-infected XL1 Blue *E. coli* were plated on LB agar plates and the plates were overlayed with nitrocellulose filters, and individual filters were screened in duplicate with a mixture of guessmer probes. After lifting the filters from the plate they were denatured for 2 min, neutralized for 5 min, and washed twice in 2× SSC for 5 min at room temperature (Sambrook et al., supra) Filters were rinsed in chloroform, blotted on 3 MM paper, and baked at 80° C. for 2 h. Baked filters were then prehybridized in 6× SSC and 10× Denhardt's solution (Sambrook et al., supra) for 2 hours at 42° C. The $^{32}$P-labeled probes Were boiled and added to hybridization buffer (1M NaCl, 50 mM Tris pH 7.4, 2 mM EDTA, 10× Denhardt's, 0.5% SDS, and 70 mg/ml salmon sperm DNA).

Prehybridized filters were transferred to the hybridization buffer containing the probe and were incubated for 12 to 16 hours at 42° C. Filters were then washed in buffer 11M NaCl, 50 mM Tris (pH 8.6), 2 mM EDTA, 1% SDS) (with 2 changes of buffer), buffer 2 (0.5M NaCl, 25 mM sodium phosphate pH 6.5, 0.5% SDS), and buffer 3 (0.5M NaCl, 50 mM sodium phosphate pH 8.5, 2 mM EDTA, 0.5% SDS), each for 2 hours at 55° C. Filters were then subjected to autoradiography. Rescreened plaques that were scored as positive on duplicate filters were isolated, replated on LB agarose plates, and rescreened with each of three guessmer probes individually. Plaques that were scored as positive with two or more probes were plaque purified. These included phages H3, H12, and P5, with H and P representing plaques isolated from the hepatoma and platelet libraries, respectively. All three of the clones bound to guessmer probes 1 and 2. Phage DNA was isolated, and the inserts were excised by restriction digestion. All phage cDNA clones were subcloned into the polykinkers of "pBLUE-SCRIPT II" KS+ or SK+ (Stratagene) or the filamentous phage M13mp13. Sequencing reactions were performed according to the "SEQUENCE" version 2.0 DNA sequencing Kit manual (US Biochemicals) with oligonucleotide primers and denatured double-stranded plasmid DNA templates or single-stranded M13 DNA.

The deduced amino acid sequence of H12 contained the deduced amino acid sequences of guessmer probes 1 and 2, as well as the amino acid sequence of peptide 32. Additional clones were obtained by multiple screenings of a polydT-primed human teratocarcinoma NTera-2D1 cell lgt10 cDNA library (Skowronski et al., 1988, Mol Cell Biol 8, 1385–1397), a polydT-primed Hela cell lgt10 cDNA library, and a random-primed HeLa lgt10 cDNA library. Probes were gel-purified restriction fragments labeled by random priming (Amersham Multiprime DNA labeling system) or overlapping 30-base oligonucleotides labeled by 5' to 3' repair with Klenow fragment (Sambrook, et al., supra). The restriction fragments were prehybridized (1 to 2 h) and hybridized (16 h, 60° C.) in 6× SSC, 5× Denhardt's solution, 0.2% SDS, and 100 mg/ml denatured salmon sperm DNA. Filters were washed twice in 2× SSC, 0.5% SDS at 60° C. for 30 min, and then three times in 0.2× SSC, 0.1% SDS at 60° C. for 30 min. Positive phage were plaque purified and phage DNA isolated by a CTAB method (Manfioletti and Schneider, 1988, Nucl Acids Res 16, 2873–2884) or with PhageSorb matrix (Promega).

Generation of recombinant H12 fitsion protein and production of antibodies.

The H12 sequence was excised from "BLUESCRIPT KS" by digestion with Eco RI and inserted in-frame into the EcoRI site of an *E. coli* expression vector (TP-7) that is based on the T7 expression system. The resultant plasmid CYP7-H12 was used to transform *E. coli* strain HMS 174 (DE3). The cells were then grown at 37° C. in terrific broth (Sambrook et al. supra) plus 50 ug/ml ampicillin to an optical density of 1.0 at 600 nm, and then induced for 2.5 hours with isopropyl b-D-thiogalactoside (IPTG) at a final concentration of 0.25 mg/ml. The bacterial pellets were harvested by centrifugation and resuspended in solution A [10 mM Tris-HCl (pH 7.9); 25% sucrose; 100 mM KCl; 2 mM DTT; 2 mM PMSF; 2 mM sodium metabisulfite). Solution B (300 mM Tris-HCl, pH 7.9; 100 mM EDTA; 4 mg/ml lysozyme) was added, and extracts were incubated for 10 min on ice. Solution C (1M LiCl; 20 mM EDTA; 0.5% NP 40) was added to the bacterial suspension, which was then sonicated on ice with three 10-s pulses at a setting of 5 (Branson). The inclusion bodies containing the H12 fusion protein were pelleted by centrifugation and washed once with solution D (10 mM Tris-HCl, pH 7.9; 0.1 mM EDTA; 0.5M LiCl; 0.5% NP 40; 1 mM DTT; 1 mM PMSF; 1 mM sodium metabisulfite) and twice with solution E (same as solution D except without the LiCl). The pellets were disrupted by sonication at each wash step. SDS sample buffer was added, and the pellets were heated at 100° C. for 5 min and subjected to electrophoresis on an SDS polyacrylamide (7%) gel. Approximately 80% of the protein in the final pelleted fraction was the H12 fusion protein, which was judged to be approximately 80 kD. The identity of the recombinant protein was confirmed by amino acid sequencing of tryptic peptides by the methods described above.

A comparable preparation of H12 fusion protein was produced, and the final pelleted fraction was resuspended in 20 mM Tris-HCl (pH 7.9), 50 mM KCl, 1 mM EDTA, 10 mM $MgCl_2$. 20% glycerol, 1 mM DTT. The H12 fusion protein was solubilized by addition of NaOH to a final concentration of 50 mM and heating to 65° C. for 10 min. The preparation was then neutralized by addition of Tris-HCl (pH 7.5) to 0.1M and HCl to 50 mM, leaving approximately 80 to 90% in the soluble fraction. This preparation was used for production of antibodies to recombinant H12 in mice and rabbits. Antibodies were produced by Berkeley Antibody Company (BAbCO) with the use of standard procedures.

Detection of HCF in variously processed HeLa extracts with antibodies to native and recombinant H12 by immunoblotting.

HeLa nuclear extracts and WGA preparations were prepared as described above. For whole-cell HeLa extracts, cells were grown on 100-mm plates in DMEM supplemented with 10% FBS and pennicillin-streptomycin, washed with PBS, and lyced in 1 ml of SDS sample buffer (5×) without bromophenol blue. The lysed cells were scraped from the plate, transferred to a microfuge tube, sonicated with a microtip at setting 2 for two 5-s pulses, and centrifuged at 12,000 g for 2 min. SDS sample buffer (5×) containing bromophenol blue was added to all extracts, and samples were subjected to electrophoresis on an SDS polyacrylamide (7%) gel. Proteins were transferred to nitrocellulose (transfer buffer, pH 8.3: 192 mM glycine, 25 mM Tris base, 0.01% SDS), and immunoblotting was performed as described (Sambrook et al., supra). Antisera to native HCF and H12 were used at a 1:200 dilution, and immunoreactive proteins were visualized by the alkaline phosphatase method (Sambrook et al., supra).

Disruption of the VP16-induced complex by addition of antibodies to recombinant H12 fusion protein.

The EMSA was performed with a WGA fraction as the source of HCF essentially as described above, except that preimmune sera and various dilutions of immune sera (diluted with preimmune sera) were incubated with protein extracts for 15 min at room temperature prior to addition of the remainder of the assay reagents.

Co-immune precipitation of a VP16-HCF complex from HeLa cell extracts.

HeLa cells were grown on 100-mm plates in DMEM plus 10% FBS. For production of cell extracts, the culture medium was removed, and cells were washed with ice-cold PBS, incubated on ice for 30 min in lysis buffer (250 mM NaCl, 0.1% NP40, 50 mM HEPES pH 7.9), transferred to a microfuge tube, and centrifuged for 2 min to remove cell debris. Preclearing of the lysate was accomplished by incubation of extracts with 50 ml of preimmune serum for 60 min at 0° C. and then with a 50-ml pellet of formalin-fixed Staphylococcus A cells for 30 min at 0° C. Extracts were then centrifuged at 12,000 g for 5 min to remove the Staph A cells. Ascites containing an antibody to VP16 (LP1; 5 ml per $10^6$HeLa cells, McLean et al., (1982) J Gen Virol 63:297–305) was added to the supernatant, which was then incubated at 0° C. for 1 h. To harvest the immune complexes protein A-Sepharose (Sigma; 100 ml of a 10% slurry) was added, and lysates were incubated at 4° C. with agitation. Protein-A beads carrying the immune complexes were collected by centrifugation at 4° C. in a microfuge for 20 sec at 10,000 g and washed three times with lysis buffer. After the final wash, SDS sample buffer was added, and the beads were heated to 100° C. for 5 min and pelleted by centrifugation. The protein-containing supernatants were subjected to SDS PAGE on a 7% gel, and coprecipitiating HCF polypeptides were detected by immunoblotting with antibodies to recombinant HCF and visualized with $^{125}$I-labeled protein A.

For infection with HSV-1, HeLa cells were treated with cycloheximide (0.1 mg/ml in DMEM with 10% serum) for 30 min and then either mock-infected or infected with HSV-1 (multiplicity of infection=5) in DMEM with 2% serum and cycloheximide (mock-infected cells were treated in an identical manner except that addition of virus was omitted). After 1 h, the virus-containing medium was aspirated, and cells were washed with DMEM plus cycloheximide and incubated at 37° C. for 2 to 3 hours in DMEM plus 10% serum and cycloheximide. Extracts were produced and immune precipitation and immunoblotting were carried out as described above for the VP16-supplemented HeLa extracts.

HCF ACTIVITY IS CONSERVED BETWEEN MAMMALS AND INSECTS.

Figure 1:
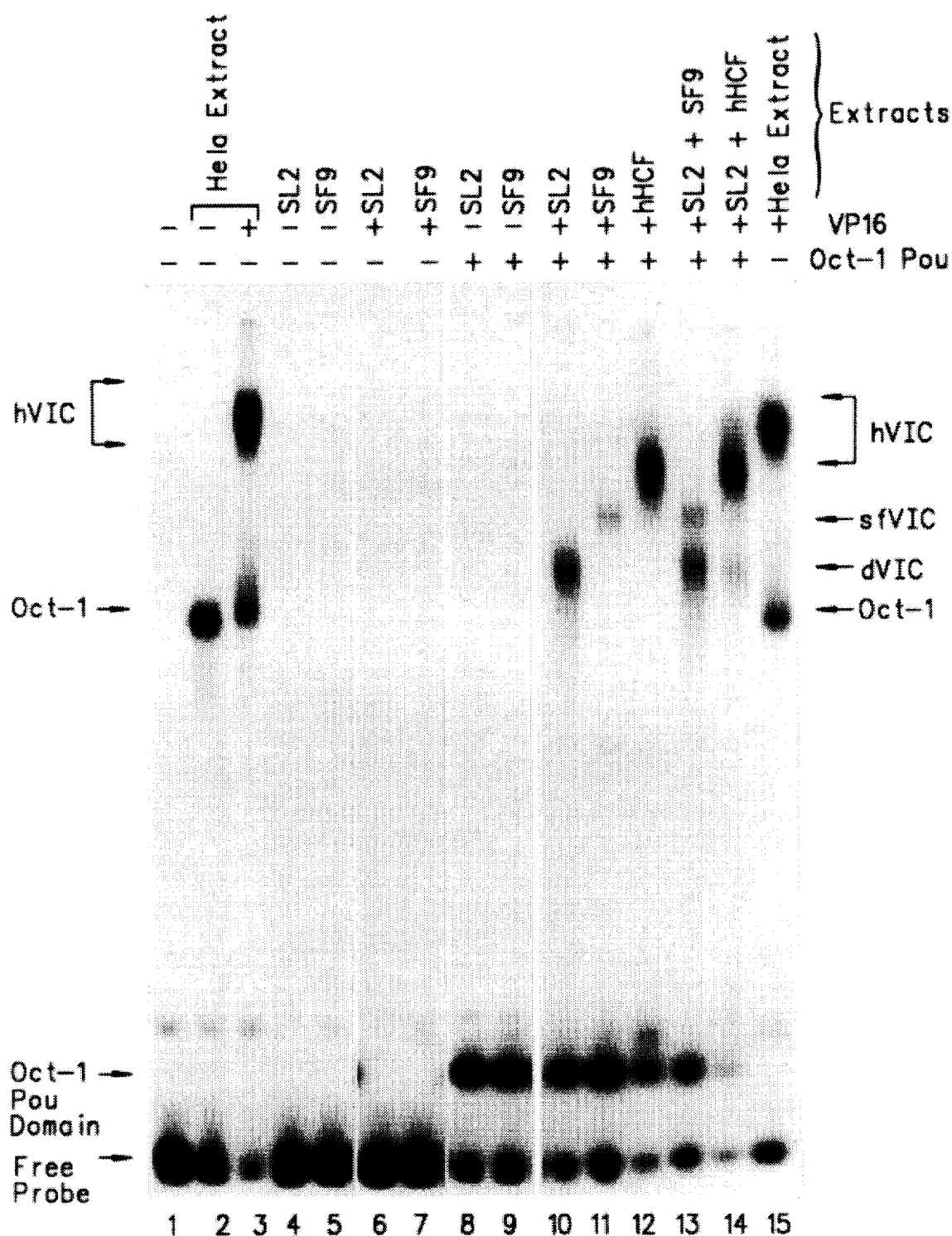
FIG. 1. Drosophila, Spodoptera, and human HCF give rise to VP16-induced complexes of different mobility. Whole cell extracts from Drosophila SL2 cells and Spodoptera Sf9 cells were tested for HCF activity by gel mobility-shift assay. Labelled (octa+)TAATGARAT probe was incubated on its own (lane1), with HeLa nuclear extract (lane 2) or with HeLa nuclear extract and VP16 (lane3) to indicate the relative mobilities of the unbound probe and the VP16-induced complex. Drosophila and Spodoptera extracts were assayed pairwise in lanes 4 to 11, on their own (lanes 4 and 5), with recombinant human Oct-1 POU (lanes 6 and 7), with GST-VP16 (lanes 8 and or with both Oct-1 POU domain and GST-VP16 (lanes 10 and 11). In lane 12 partially purified human HCF, which is devoid in Oct-1 activity, was incubated with both Oct-1 POU domain and GST-VP16. The Drosophila extract was mixed with the Spodoptera extract (lane 13) or human HCF (lane 14) and incubated for 10 mins at 30° C. and prior to assembly of gel-mobility shift reactions that included Oct-1 POU domain and GST-VP16.

HCF has been characterized in part by EMSAs. When nuclear extracts from mammalian cells are incubated with a probe containing the (Octa$^+$)TAATGARAT motif from the herpes virus ICP0 gene promoter a single protein-DNA complex is observed that corresponds to binding of the cellular factor Oct1 (FIG. 1, compare lanes 1 and 2). If VP16 is included in the reaction a second, more slowly migrating complex is observed (lane 3). Several studies have shown that this VP16- induced complex (VIC) consists of Oct1, VP16, and one or more additional factors termed HCF. HCF activity has also been identified in insect cells (Kristie et at., 1988). When whole cell extracts from the *Drosophila melanogaster* SL2 cell line or the fall army worm *Spodoptera frugiperda* Sf9 cell line were incubated with the (Octa+)TAATGARAT probe, recombinant human Oct1 POU domain and VP16, a novel complex was detected (lanes 10 and 11). Formation of this complex was dependent on the addition of both VP16 and Oct1 POU domain, as no specific complexes were observed if the extracts were incubated with the probe alone (lanes 4 and 5) or mixed individually with the Oct1 POU (lanes 6 and 7) or with VP16 (lanes 8 and 9). The VIC formed with partially purified human HCF (see below) is also shown (lane 12). A striking feature was the distinctive mobilities of the VP16-induced complexes incorporating HCF from the different organisms. Under our assay conditions and in contrast to previous reports, HCF from Sf9 cells yielded a faster migrating complex than did HCF from human HeLa cells.

Little has been published about the stoichometry of the VIC. In particular, the nature of HCF has not been charaterized nor has not been known whether HCF corresponds to one or several factors. A convenient assay for monitoring the oligomerization state of DNA binding proteins has been to mix full-length and truncated forms of the protein, and then determine by EMSA whether heteromeric complexes of novel mobility can be generated (Hope & Struhl). As a variation of this technique, we mixed HCF obtained from different organisms to ask whether multiple HCF factors are incorporated into the VP16-induced complex. When the Drosophila extract was mixed with the Spodoptera extract (lane 13) or human HCF (lane 14) additional (intermediary) complexes were not detected. These results may suggest that there is only a single HCF factor in each VIC. However, they do not exclude the possibility that HCF activity comprises multiple components, and either the subunits cannot be mixed across organisms or the complex is particularly stable. In any case, these results indicated that HCF is a well-conserved activity.

PURIFICATION OF HUMAN HCF

One method of isolating cDNA clones that encode proteins identified by a particular function is by obtaining peptide sequence from the purified proteins, which is used to derive oligonucleotide probes for screening cDNA libraries. With respect to HCF, the our data suggested to us a number of advantages to this approach. First, the number of polypeptides and/or other compounds needed to reconstitute HCF activity was not known. The extemely slow relative mobility of the VIC, the sensitivity of HCF to inactivation by heat and chemical denaturation all suggested that HCF activity consisted of a multisubunit complex. If this were the case, a cloning strategy based on bacterial expression or phage display would be unlikely to succed. Secondly, the identity of any isolated cDNA clones could be confirmed directly by comparison of the predicted amino acid sequence with the actual peptide sequence, an important criteria if the identifying function could not be regenerated from individual cDNAs.

We purified HCF from HeLa cells to near homogeneity using two related schemes (see Experimental:Procedures). The procedure outlined in detail below used a combination of affinity and conventional chromatograpic steps plus glycerol gradient sedimentation (also see FIG. 2). HCF activity was monitored by EMSAs using recombinant Oct1 POU and GST-VP16ΔC and could be correlated throughout the purification with a set of at least eight polypeptides that ranged in apparant molecular weight from 110 to 300 kD.

Preliminary studies showed that HCF, like certain other nuclear regulatory proteins, is modified with multiple N-acetyl glucosamine (GlcNAc) sugar residues and can be bound to wheat germ agglutinin (WGA) beads. Because the majority of proteins (>99%) in a typical nuclear extract are not retained by lectin columns (Jackson and Tjian, 1989), WGA affinity chromatography used as an initial purification step gave substantial enrichment of HCF activity. By mixing fresh nuclear extracts with WGA agarose beads at a high salt concentration (0.42M) and 0.5% NP40, we could routinely bind and then recover by competition with the free GlcNAc, about 80 to 90% of HCF activity. This single step gave a 200-fold purification. Use of a fresh extract was critical, as a significant fraction of active HCF (up to 60%) failed to bind to the WGA affinity column if the crude nuclear extract had been frozen or dialysed. We suspect that this is because of deglycosylase activities in the extract that remove or modify enough sugar residues to substantially reduce the affinity of HCF for WGA.

A sizable proportion of Oct1 (40–50%) is also glycosylated (Pierani et al., 1990, Mol Cell Biol 10, 6204) and copurified with HCF. This contaminating Oct1 complicated quantitation of HCF activity in subsequent steps because the endogenous native Oct1 appeared to be incorporated into the VIC more efficiently than recombinant Oct1 POU. It had been shown that, although both HCF and Oct1 bind to double-stranded DNA-cellulose, the two activities could be differentially eluted with a salt gradient (Katan et al., 1989). Therefore, after HCF was eluted from the WGA column, the peak protein fractions were loaded directly onto a DNA-celluose column pre-equilibrated with buffer D containing 50 mM KCl, and the column developed with a linear KCl gradient (0.05 to 0.5M). HCF eluted early in the gradient (between 75 and 100 mM KCl), while Oct1 eluted at a higher salt concentration (>180 mM). This chromatographic step gave a further 50-fold purification and removed many DNA-binding proteins that required higher salt concentration for elution.

Figure 2A:
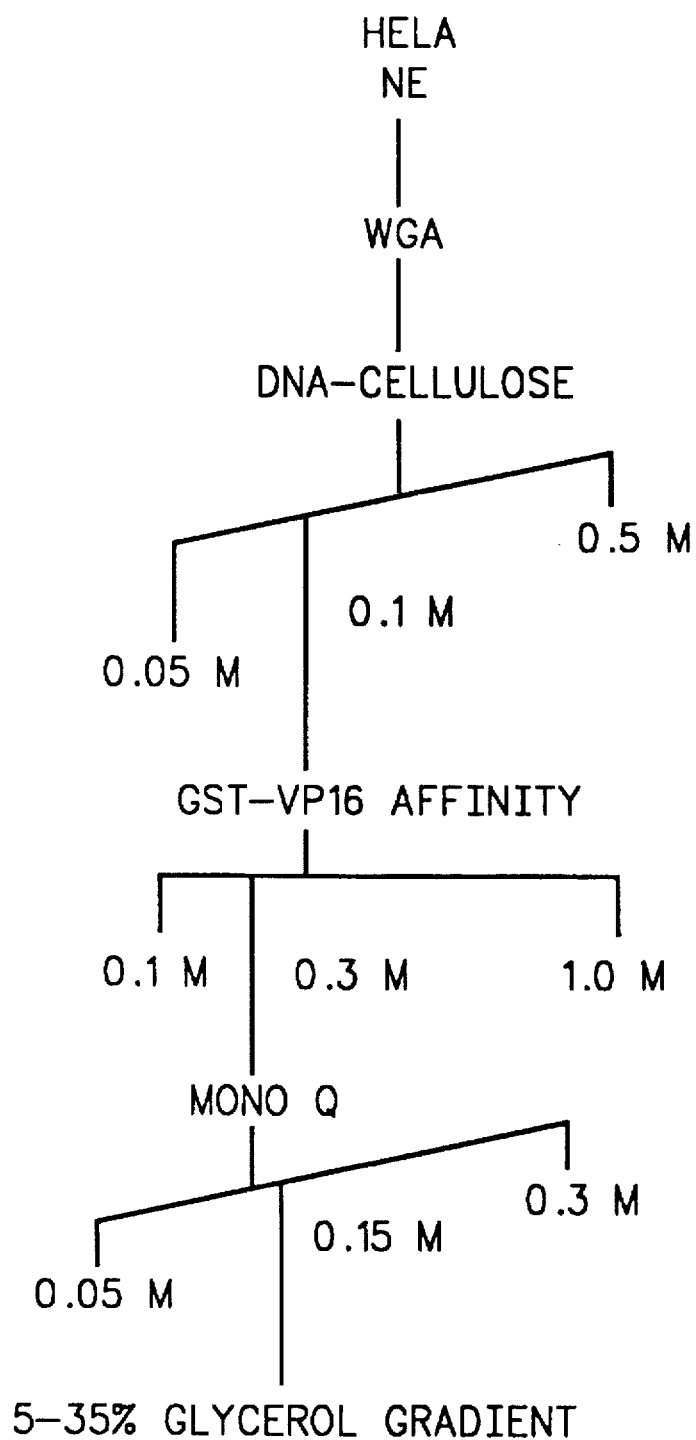
FIGS. 2(A)–2(D) Purification of human HCF.
Figure 2B:
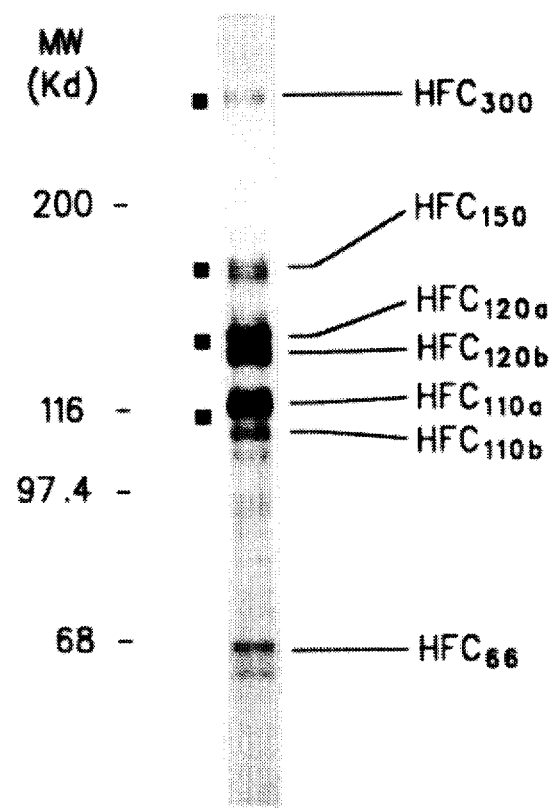
Figures 2C, 2D:
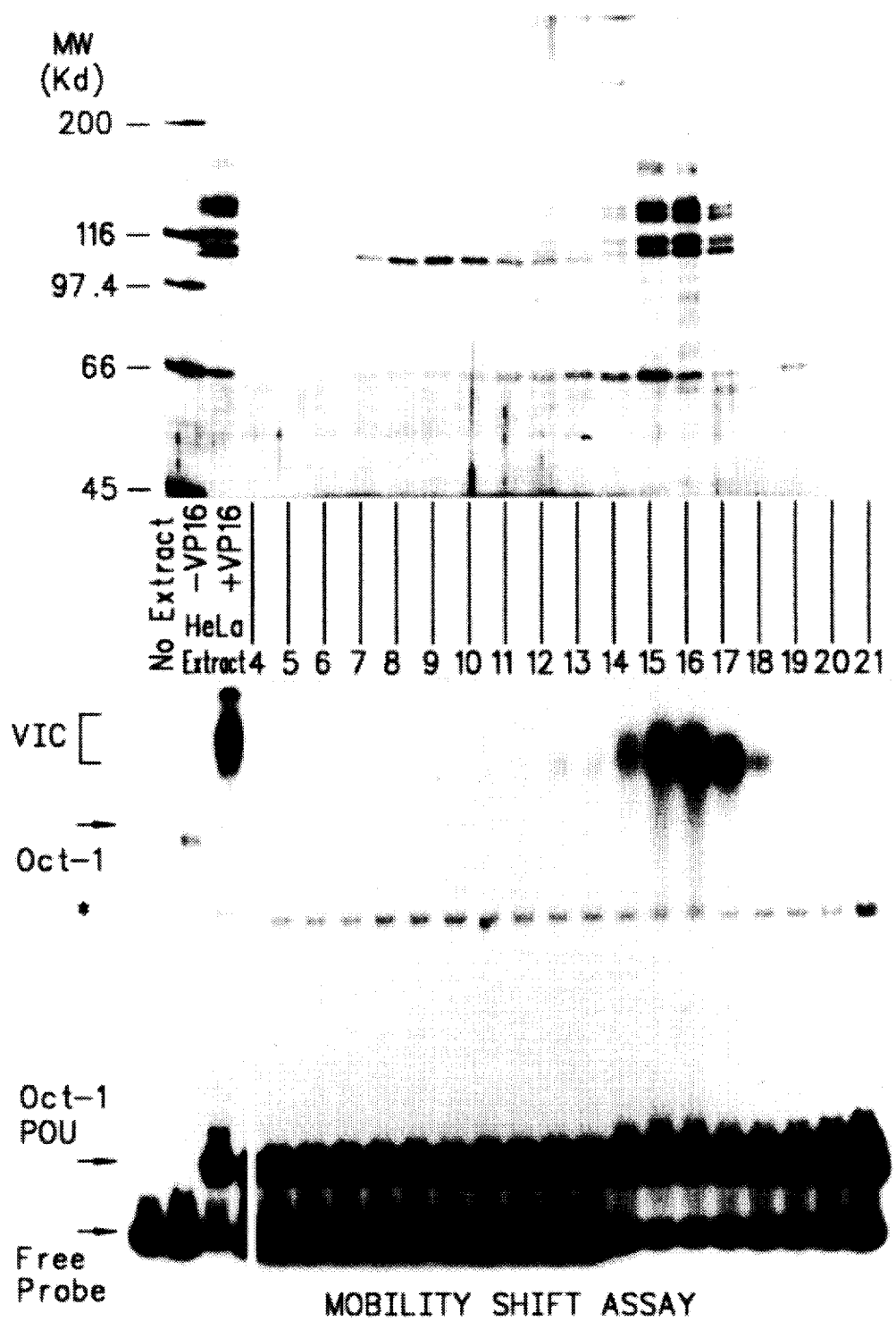

A notable feature of HCF is its ability to complex with VP16 independently of Oct1 or specific DNA. This allowed us to use an affinity resin that had GST-VP16αC bound to glutathione-agarose beads in the purification of HCF. The background of nonspecifically bound protein was lower with the GST system than with either VP16 covalently linked to activated "SEPHAROSE" beads or with a VP16-protein A fusion bound to IgG-agarose beads. The peak HCF-containing fractions from the DNA-cellulose column were pooled, adjusted to 100 mM KCl, and mixed batch-wise with GST-VP16αC -loaded glutathione agarose beads. The beads were then poured into a column and washed, and HCF was eluted with 300 mM KCI. GST-VP16αC remained bound to the beads under these conditions and could not be detected in the eluate by EMSA. SDS PAGE and subsequent silver-staining of the eluted proteins revealed a patten that was nearly identical to that shown in FIG. 2B. Fractions that contained HCF activity were pooled and concentrated with the use of "MONO Q" HPLC, which also removed some minor contaminants, and then subjected to glycerol gradient sedimentation. Proteins in the gradient fractions that were separated by SDS PAGE and silver-stained are shown in FIG. 2, panel C, while panel D shows the same fractions assayed for HCF activity by EMSA. HCF activity peaked in fractions 14 to 17 and correlated with a series of polypeptides clustered at 150 kD, 120 kD and 110 kD. Although the 300-kD polypeptide peaked in fractions 14 and 15, very little was detected in the most active fractions (16 and 17). The 66-kD polypeptide was probably a breakdown product, as its relative abundance varied among preparations. The major polypeptide of approximately 110 kD did not cosediment with activity and thus appeared to be a contaminant.

On the basis of protein standards applied to a parallel gradient, we estimated a sedimentation coefficient for HCF of approximately 5S. The purified HCF was also subjected to gel filtration chromatography and based on elution time was estimated to have a molecular weight of 450 to 650 KD.

We obtained a polypeptide profile similar to that provided by the glycerol gradient by subjecting WGA-purified HCF to chromatography first on a "MONO S" column and then on a "MONO Q" column (see Experimental Procedures). These three purification steps yielded proteins of 300, 150, 120, and 110 kD. Because the same pattern of polypeptides copurified through a collection of diverse chromatographic steps, we believed that most of the major polypeptides were related to HCF activity. In fact, this distinctive banding pattern was apparant in the peak activity fractions after DNA-cellulose chromatography. We therefore decided to obtain amino acid sequence from each of the observed polypeptides.

SEQUENCING OF PEPTIDES DERIVED FROM PUTATIVE HCF POLYPEPTIDES

Proteins in the most purified HCF fractions were separated by SDS PAGE and transfered to a PVDF membrane. Individual protein bands were excised after staining the membrane with Ponceau S and digested in situ with either trypsin or lys-c. The resulting peptides were separated by HPLC, and selected peptides were sequenced by Edman degradation. Protein bands in the HCF sample used for lys-c digestion were sufficiently well resolved so that the bands corresponding to the two major polypeptides from the 120 kD and 110 kD clusters (termed p120a, p120b, p110a, and p110b respectively, see FIG. 2B) could be isolated individually. The HPLC profiles of lys-c-generated peptides from the 150 kD doublet, p120a, p120b, and p110a were extremely similar, suggesting that the parent polypeptides were closely related. Although the peptide profile for p110b was more complex, there still appeared to be many peaks in common with the previous profiles. We suspect that the extra peptides were derived from the contaminating 110 kD polypeptide that did not correlate with activity after glycerol gradient sedimentation (see FIG. 2C). Only a small amount of the 300-kD polypeptide was able to be transfered to the PVDF membrane, probably owing to its large size, and thus gave insufficient peptide yields for amino acid determination. Direct amino-terminal sequencing was also unsuccessful probably as a result of modification of the terminus.

To confirm that the p150, p120a, p120b, p110a, and p110b polypeptides were related to each other as suggested by their similar HPLC profiles, we selected two well resolved peaks that appeared to be common to each digestion. The deduced amino acid sequences (FIG. 3) were identical in nearly every case, and differed only at ambiguous residues. This argues strongly that the majority of these polypeptides are encoded by the same gene and that the protein heterogeneity is generated at the level of mRNA processing or post-translational modification. Sixteen additional peptide sequences were also obtained.

ISOLATION OF cDNAS THAT ENCODE HCF

Using the peptide sequence obtained from the purified protein, we designed three guessmer probes and used them to screen a human hepatocyte and a human platelet cDNA library. Three recombinant bacteriphages (1H-3, 1H-12, and 1P-5) gave positive signals when hybridized with two of the three guessmers. The inserts of recombinants H-3 and H-12 were cloned and sequenced and found to contain overlapping open reading frames. Inspection of the deduced amino acid sequence revealed the peptide sequences corresponding to the two hybridizing guessmers. In addition, the ORF encoded a third peptide sequence that we had obtained from the purified HCF protein, but had not been used to design a guessmer for library screening. These results suggest that these cDNA inserts were derived from the gene encoding the protein we had purified and sequenced.

The H-3 insert was then used as a probe to screen additional cDNA libraries at high stringency. Multiple overlapping clones were isolated that together gave a composite cDNA of about 5.3 kb. The ORF was terminated by a nonsense codon (UGA) ten amino acids downstream of pep-12, but remained open upstream. Because Northern (RNA) blot analysis with total HeLa RNA detected a single 9.5 to 10 kb transcript and many peptide sequences remained unaccounted for, we extended the composite cDNA by repeated rounds of screening with probes derived from the 5' most sequences after each round. A weak polyadenylation signal (5" AAUUAAAA3') was found 1791 bp downstream of the 3' end of the ORF and was followed 12 bp later by a stretch of 15 A's, presumably part of the poly A tail. No other cDNAs further extended the 3' end, suggesting that this was the bona fide 3' end of the transcript. Southern Blotting analysis of human DNA at reduced stringency indicated that the cDNA is derived from a single copy gene.

Sixteen other peptide sequences were encountered (see FIG. 3A). The complete ORF is notably GC-rich. A number of functionally significant features are apparent from the disclosed amino acid sequence of HCF (SEQ ID NO: 05). For example, shown boxed in FIG. 3c are 8 copies of a 26 amino acid repeat sequence: (SEQ ID NO: 06), (SEQ ID NO: 07), (SEQ ID NO: 08), (SEQ ID NO: 09), (SEQ ID NO: 10), (SEQ ID NO: 11), (SEQ ID NO: 12), (SEQ ID NO: 13) and (SEQ ID NO: 14), respectively "THE TNT" consensus sequence (SEQ ID NO: 15) also shown in FIG. 3e. The 2 cysteines and 1 histidine in each repeat define a metal binding domain. This structure presents a target for compounds which specifically disrupt protein-protein interaction domain or a protein-DNA interface. By disrupting the interaction between repeats of HCF and VP16, Oct1 or DNA, such compounds could inhibit VP16 function and form the basis of a drug against HSV.

The position of the repeat sequences within HCF indicates that they are the recognition motif for a site-specific protease, and that their scission produces the spectrum of HCF polypeptides observed in the cell. These repeat sequences have not been described in any known protein and thus represent the progenitor of a new family of site-specific protease recognition sites. Accordingly, such sequences are usefully incorporated into other proteins to achieve a novel site-specific cleavage, e.g. one that converts a pro drug into a drug or inactivates an existing drug.

Other apparent structural regions within the HCF sequence include: clusters of the bulky hydrophobic residues tryptophan, phenylalanine and tyrosine from amino acids 19–384 & 1812–1999; clusters of the basic residues lysine and arginine from amino acids 426–875; clusters of the acidic residues aspartic acid and glutamic acid from amino acids 1445–1753; and a strongly alpha helical region from amino acids 1609–1647. These regions constitute targets for disruption of protein-protein or protein-DNA interactions including those with VP16 and Oct1.

ALTERATION OF VIC FORMATION BY ANTIBODIES TO NATIVE AND RECOMBINANT HCF

As a means of deciphering whether the cDNA we isolated encoded a protein related to the HCF in the VIC, we sought to obtain antibodies to a fragment of the cDNA encoded recombinant protein and test whether they disrupted or altered the mobility of the VIC. The H-12 cDNA insert was subcloned into a plasmid vector for expression of the encoded protein in E. coli. A recombinant protein of approximately 80 kD was produced, isolated from inclusion bodies, and injected into animals for antibody production. EMSAs were performed whereby various dilutions of preimmune and immune sera were incubated with a WGA fraction containing HCF activity prior to addition of the assay reagents (FIG. 4). As a comparison, antiserum raised against HCF purified from HeLa nuclei was also tested, along with a monoclonal antibody to VP16 and a control antibody. Antibodies to purified HCF disrupted VIC formation at high concentrations and altered its mobility at lower concentrations, while preimmune serum had no effect, indicating that the most purified protein fraction contained HCF. Antibodies to recombinant HCF disrupted the VIC at dilutions of 1:10, 1:100, and 1:500. The 1:5000 dilution only slightly shifted the VIC, as did the preimmune serum. These results indicate that the isolated cDNA encodes at least a component of HCF.

RECOGNITION OF MULTIPLE FORMS OF HCF BY ANTIBODIES TO RECOMBINANT HCF

Purification of HCF from HeLa nuclei yielded a collection of protein products, at least some of which contained related peptides (FIG. 3). However, we had been unable to obtain amino acid sequence from the largest (300 kD) polypeptide and were therefore unable to determines its relatedness to the lower molecular weight components. As a means of determining which of the purified species were related to recombinant HCF we performed immunoblots with variously processed HeLa cell extracts.

As seen in FIG. 5, antisera to both native and recombinant HCF recognized E. coli-produced recombinant HCF (H-12), the 300-kD protein in HeLa nuclear extracts and WGA extracts, and the three groups of proteins at the 150-, 120-, and 110-kD regions of the gel.

These results indicated that the 300-kD protein was related to the recombinant HCF as well as to a number of the lower molecular weight HCF species. However, it was still unclear as to whether the multiple HCF components were produced in vivo and thus possibly functionally relevant, or whether their generation was an artifact of our purification protocol. Therefore, we grew HeLa cells in culture, and lysed them directly in SDS sample buffer; the extracts were subjected to electrophoresis on an SDS polyacrylamide (7%) gel and immunoblotting with antibodies to recombinant and native HCF. As shown in FIG. 5, panel C, the 150-, 120-, and 110-kD proteins were present, suggesting that these species are generated in vivo. The 300-kD protein was not apparent in the whole-cell extracts.

CO-IMMUNE PRECIPITATION OF VP16 AND HCF POLYPEPTIDES FROM HELA EXTRACTS

The observations that HCF facilitates complex formation between VP16, Oct1, and TAATGARAT and binds to a VP16 affinity column suggest that HCF and VP16 interact directly in vitro. We next sought to ascertain whether VP16 and HCF could be co-immune precipitated from a HeLa whple cell extract. HeLa monolayers were lysed in lysis buffer, and the extracts were supplemented with GST-VP16 delta C and incubated with an antibody to VP16 (LP 1; McLean et at, supra). The immune complexes were isolated with protein A-Sepharose, heated to 100° C. in SDS sample buffer, and separated by SDS PAGE. HCF polypeptides that co-immune precipitated with VP16 were visualized by immunoblotting with antiserum to rHCF. Only from the VP16-supplemented extracts could the 300-, 150-, 120-, and 110-kD forms of HCF be co-immune precipitated with the VP16 antibody. Identical membranes were immunoblotted with antisera to three other nuclear proteins (NFkB p50, TATA binding protein, and c-Jun); none of the three could be co-immune precipitated with antibody to VP16, suggesting that the VP16-HCF interaction is specific. When VP16 is delivered to HeLa cells via infection with HSV-1, the HCF polypeptides could also be co-immune precipitated with the VP16 antibody.

DISCUSSION

HCF activity is necessary for allowing stable interaction of VP16, Oct1, and the HSV IE gene regulatory element TAATGARAT in vitro. Because VP16 carries out its transcriptional activation function only when tethered to DNA, the presence of HCF appears crucial for activation of HSV IE genes in vivo. When EMSAs are performed there is no apparent Oct-1-HCF-DNA complex; this, along with the the observation that HCF binds to a VP16 affinity column in the absence of Oct1 suggests that HCF interacts directly with VP16, but not with Oct-1, at least not in the absence of VP16. One possibility is that HCF interacts with VP16 and renders it competant to bind to Oct1. The complex then in turn can contact IE gene regulatory sequences.

HCF activity consists of a collection of polypeptides of 110, 120, 150, and 300 kD encoded by a single structural gene that gives rise to a parent protein of 2039 amino acids. This parent protein appears to be processed in vivo to yield multiple immunologically related forms of HCF that correspond in molecular weight to the polypeptides we observed during purification of HCF activity. The deduced amino acid sequence of the full-length HCF clone contains 6 threonine-rich repeats that are potential sites of phosphorylation. These repeated motifs are positioned such that proteolytic processing within the repeats generates proteins of the sizes we observed in purified HCF fractions. Thus, the regulated processing at the repeats is responsible for generating various components of HCF activity.

HCF allows formation of a stable HCF-VP16-Oct-1-TAATGARAT complex in vitro. However, HCF is shown to be present in a number of mammalian cell lines and is conserved throughout evolution from insects to humans. During fractionation HCF polypeptides appear in multiple fractions on a number of diverse columns, rather than as a distinct peak of activity. This indicates that HCF interacts with a variety of nuclear proteins and participates in the assembly of multiple protein-DNA regulatory complexes in vivo.

Use of HCF in drug screening assays.

Corning ELISA strip wells (8 wells per strip) were coated with avidin (1.0 ug per well) by incubating avidin (200 ul of a 5 ug/ml stock) in coupling buffer (per liter: 1.6 g $Na_2CO_3$, 2.9 g, $NaHCO_3$, 0.9 g $NAN_3$) on the well for 12 h at 4° C. The buffer was decanted, and nonspecific binding sites on the wells were blocked with 1% skim milk in phosphate-buffered saline (PBS) for 1 h at 37° C. Blocking buffer was discarried, and the TAATGARAT-containing oligonucleotide (1 pmol/well) was added to the wells and incubated for 30 min at room temperature. The oligonucleotide was double-stranded and contained a biotin tag on the sense strand.

The oligo-containing solution was then removed, and the wells were washed with 1% milk in PBS. VP16 engineered to contain the heart muscle kinase phosphorylation site (HMK-VP16) was labeled with $\lambda^{32}P$-ATP and mixed with recombinant Oct1-POU domain and partially purified HCF, all in HEG buffer (0.1M KCl, 25 mM HEPES pH 7.9, 0.5 mM EDTA, 20% glycerol, 0.01% LDAO, 0.1M AEBSF, 0.1M Na metabisulfite, 10 mM β-mercaptocthanol) plus 200 ug/ml bovine serum albumin (BSA).

The protein mixture was then added to the prepared wells and incubated for 30 min at room temperature. Samples were then removed, and the wells were washed three times with the PBS/milk solution. Wells were separated and put into scintillation vials, scintillation cocktail was added, and samples were counted in a liquid scintillation counter.

Binding of VP16 to the wells was found to be dependent on the presence of Oct1, HCF, and TAATGARAT-containing oligonucleotide. Small molecules are introduced into the assay, and those that inhibit binding of $^{32}P$-VP16 purified, characterized and applied diagnostically and therapuetically as disclosed herein.

It is evident from the above results that one can use the methods and compositions disclosed herein for making and identifying diagnostic probes and therapeutic drugs. VP16 is a viral transcriptional activation protein that on its own is not a site-specific DNA binding protein but rather requires the HCF, to be recruited to the DNA. In addition to Herpes Simplex Virus, several other human viral pathogens such as Adenovirus, Herpes Zoster Virus, Cytomegolavirus, Ebstein-Barr Virus and Hepatitis B Virus have transactivator proteins that, like VP16, are not by themselves site-specific DNA binding proteins. Occupying a central role in the recruitment of viral transactivators to DNA, HCF provides a key ingredient in the identification, design, and production of useful drugs against these human pathogens.

It will also be clear to one skilled in the art from a reading of this disclosure that advantage can be taken to effect alterations of gene expression: both genes encoding HCF and genes amenable to HCF-mediated transcriptional modulation, especially viral genes. Such alterations can be effected for example, using a variety of gene therapy protocols.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

ATGCTAATGA RAT                         1 3

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GAGAACCAGT GGTTTGATGT GGGCGTGATC AAG         3 3

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
AAGCAGGAGC  TNCAGCCTGG  CACAGCCTAC  AAG                          33
```

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

```
ATGCTAATGA  TAT                                                  13
```

( 2 ) INFORMATION FOR SEQ ID NO:5:

( i ) SEQUENCE CHARACTERISTICS:
        ( A ) LENGTH: 2035 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Met  Ala  Ser  Ala  Val  Ser  Pro  Ala  Asn  Leu  Pro  Ala  Val  Leu  Leu  Gln
 1                   5                    10                       15

Pro  Arg  Trp  Lys  Arg  Val  Val  Gly  Trp  Ser  Gly  Pro  Val  Pro  Arg  Pro
                20                    25                  30

Arg  His  Gly  His  Arg  Ala  Val  Ala  Ile  Lys  Glu  Leu  Ile  Val  Val  Phe
          35                    40                       45

Gly  Gly  Gly  Asn  Glu  Gly  Ile  Val  Asp  Glu  Leu  His  Val  Tyr  Asn  Thr
     50                    55                  60

Ala  Thr  Asn  Gln  Trp  Phe  Ile  Pro  Ala  Val  Arg  Gly  Asp  Ile  Pro  Pro
65                   70                   75                            80

Gly  Cys  Ala  Ala  Tyr  Gly  Phe  Val  Cys  Asp  Gly  Thr  Arg  Leu  Leu  Val
                85                    90                       95

Phe  Gly  Gly  Met  Val  Glu  Tyr  Gly  Lys  Tyr  Ser  Asn  Asp  Leu  Tyr  Glu
               100                   105                 110

Leu  Gln  Ala  Ser  Arg  Trp  Glu  Trp  Lys  Arg  Leu  Lys  Ala  Lys  Thr  Pro
          115                   120                 125

Lys  Asn  Gly  Pro  Pro  Cys  Pro  Arg  Leu  Gly  His  Ser  Phe  Ser  Leu
     130                   135                 140

Val  Gly  Asn  Lys  Cys  Tyr  Leu  Phe  Gly  Gly  Leu  Ala  Asn  Asp  Ser  Glu
145                  150                   155                          160

Asp  Pro  Lys  Asn  Asn  Ile  Pro  Arg  Tyr  Leu  Asn  Asp  Leu  Tyr  Ile  Leu
               165                   170                      175

Glu  Leu  Arg  Pro  Gly  Ser  Gly  Val  Val  Ala  Trp  Asp  Ile  Pro  Ile  Thr
          180                   185                 190

Tyr  Gly  Val  Leu  Pro  Pro  Pro  Arg  Glu  Ser  His  Thr  Ala  Val  Val  Tyr
          195                   200                 205
```

-continued

| | | | | | | | | | | | | | | |
|---|---|---|---|---|---|---|---|---|---|---|---|---|---|---|
| Thr | Glu 210 | Lys | Asp | Asn | Lys 215 | Lys | Ser | Lys | Leu | Val 220 | Ile | Tyr | Gly | Gly | Met |
| Ser 225 | Gly | Cys | Arg | Leu | Gly 230 | Asp | Leu | Trp | Thr | Leu 235 | Asp | Ile | Asp | Thr | Leu 240 |
| Thr | Trp | Asn | Lys | Pro 245 | Ser | Leu | Ser | Gly | Val 250 | Ala | Pro | Leu | Pro | Arg 255 | Ser |
| Leu | His | Ser | Ala 260 | Thr | Thr | Ile | Gly | Asn 265 | Lys | Met | Tyr | Val 270 | Phe | Gly | Gly |
| Trp | Val | Pro 275 | Leu | Val | Met | Asp | Asp 280 | Val | Lys | Val | Ala 285 | Thr | His | Glu | Lys |
| Glu | Trp 290 | Lys | Cys | Thr | Asn | Thr 295 | Leu | Ala | Cys | Leu | Asn 300 | Leu | Asp | Thr | Met |
| Ala 305 | Trp | Glu | Thr | Ile | Leu 310 | Met | Asp | Thr | Leu | Glu 315 | Asp | Asn | Ile | Pro | Arg 320 |
| Ala | Arg | Ala | Gly | His 325 | Cys | Ala | Val | Ala | Ile 330 | Asn | Thr | Arg | Leu | Tyr 335 | Ile |
| Trp | Ser | Gly | Arg 340 | Asp | Gly | Tyr | Arg | Lys 345 | Ala | Trp | Asn | Asn | Gln 350 | Val | Cys |
| Cys | Lys | Asp 355 | Leu | Trp | Tyr | Leu | Glu 360 | Thr | Glu | Lys | Pro | Pro 365 | Pro | Pro | Ala |
| Arg | Val 370 | Gln | Leu | Val | Arg | Ala 375 | Asn | Thr | Asn | Ser | Leu 380 | Glu | Val | Ser | Trp |
| Gly 385 | Ala | Val | Ala | Thr | Ala 390 | Asp | Ser | Tyr | Leu | Leu 395 | Gln | Leu | Gln | Lys | Tyr 400 |
| Asp | Ile | Pro | Ala | Thr 405 | Ala | Ala | Thr | Ala | Thr 410 | Ser | Pro | Thr | Pro | Asn 415 | Pro |
| Val | Pro | Ser | Val 420 | Pro | Ala | Asn | Pro | Pro 425 | Lys | Ser | Pro | Ala | Pro 430 | Ala | Ala |
| Ala | Ala | Pro 435 | Ala | Val | Gln | Pro | Leu 440 | Thr | Gln | Val | Gly | Ile 445 | Thr | Leu | Leu |
| Pro | Gln 450 | Ala | Ala | Pro | Ala 455 | Pro | Pro | Thr | Thr | Thr 460 | Ile | Gln | Val | Leu |
| Pro 465 | Thr | Val | Pro | Gly | Ser 470 | Ser | Ile | Ser | Val | Pro 475 | Thr | Ala | Ala | Arg | Thr 480 |
| Gln | Gly | Val | Pro | Ala 485 | Val | Leu | Lys | Val | Thr 490 | Gly | Pro | Gln | Ala | Thr 495 | Thr |
| Gly | Thr | Pro | Leu 500 | Val | Thr | Met | Arg | Pro 505 | Ala | Ser | Gln | Ala | Gly 510 | Lys | Ala |
| Pro | Val | Thr 515 | Val | Thr | Ser | Leu | Pro 520 | Ala | Gly | Val | Arg | Met 525 | Val | Val | Pro |
| Thr | Gln 530 | Ser | Ala | Gln | Gly | Thr 535 | Val | Ile | Gly | Ser | Ser 540 | Pro | Gln | Met | Ser |
| Gly 545 | Met | Ala | Ala | Leu | Ala 550 | Ala | Ala | Ala | Ala 555 | Thr | Gln | Lys | Ile | Pro 560 |
| Pro | Ser | Ser | Ala | Pro 565 | Thr | Val | Leu | Ser | Val 570 | Pro | Ala | Gly | Thr | Thr 575 | Ile |
| Val | Lys | Thr | Met 580 | Ala | Val | Thr | Pro | Gly 585 | Thr | Thr | Thr | Leu | Pro 590 | Ala | Thr |
| Val | Lys | Val 595 | Ala | Ser | Ser | Pro | Val 600 | Met | Val | Ser | Asn | Pro 605 | Ala | Thr | Arg |
| Met | Leu 610 | Lys | Thr | Ala | Ala | Ala 615 | Gln | Val | Gly | Thr | Ser 620 | Val | Ser | Ser | Ala |
| Thr | Asn | Thr | Ser | Thr | Arg | Pro | Ile | Ile | Thr | Val | His | Lys | Ser | Gly | Thr |

|     |     |     |     |     |     |     |     |     |     |     |     |     |     |     |
| --- | --- | --- | --- | --- | --- | --- | --- | --- | --- | --- | --- | --- | --- | --- |
| 625 |     |     |     |     | 630 |     |     |     |     | 635 |     |     |     | 640 |
| Val | Thr | Val | Ala | Gln | Gln | Ala | Gln | Val | Val | Thr | Thr | Val | Val | Gly | Gly |
|     |     |     |     | 645 |     |     |     |     | 650 |     |     |     | 655 |     |
| Val | Thr | Lys | Thr | Ile | Thr | Leu | Val | Lys | Ser | Pro | Ile | Ser | Val | Pro | Gly |
|     |     |     | 660 |     |     |     |     | 665 |     |     |     |     | 670 |     |
| Gly | Ser | Ala | Leu | Ile | Ser | Asn | Leu | Gly | Lys | Val | Met | Ser | Val | Val | Gln |
|     |     |     | 675 |     |     |     |     | 680 |     |     |     |     | 685 |     |     |
| Thr | Lys | Pro | Val | Gln | Thr | Ser | Ala | Val | Thr | Gly | Gln | Ala | Ser | Thr | Gly |
|     |     |     | 690 |     |     |     | 695 |     |     |     |     | 700 |     |     |     |
| Pro | Val | Thr | Gln | Ile | Ile | Gln | Thr | Lys | Gly | Pro | Leu | Pro | Ala | Gly | Thr |
| 705 |     |     |     |     | 710 |     |     |     |     | 715 |     |     |     |     | 720 |
| Ile | Leu | Lys | Leu | Val | Thr | Ser | Ala | Asp | Gly | Lys | Pro | Thr | Thr | Ile | Ile |
|     |     |     |     | 725 |     |     |     |     | 730 |     |     |     |     | 735 |     |
| Thr | Thr | Thr | Gln | Ala | Ser | Gly | Ala | Gly | Thr | Lys | Pro | Thr | Ile | Leu | Gly |
|     |     |     | 740 |     |     |     |     | 745 |     |     |     |     | 750 |     |     |
| Ile | Ser | Ser | Val | Ser | Pro | Ser | Thr | Thr | Lys | Pro | Gly | Thr | Thr | Thr | Ile |
|     |     |     | 755 |     |     |     |     | 760 |     |     |     |     | 765 |     |     |
| Ile | Lys | Thr | Ile | Pro | Met | Ser | Ala | Ile | Ile | Thr | Gln | Ala | Gly | Ala | Thr |
|     |     |     | 770 |     |     |     | 775 |     |     |     |     | 780 |     |     |     |
| Gly | Val | Thr | Ser | Ser | Pro | Gly | Ile | Lys | Ser | Pro | Ile | Thr | Ile | Ile | Thr |
| 785 |     |     |     |     | 790 |     |     |     |     | 795 |     |     |     |     | 800 |
| Thr | Lys | Val | Met | Thr | Ser | Gly | Thr | Gly | Ala | Pro | Ala | Lys | Ile | Ile | Thr |
|     |     |     |     | 805 |     |     |     |     | 810 |     |     |     |     | 815 |     |
| Ala | Val | Pro | Lys | Ile | Ala | Thr | Gly | His | Gly | Gln | Gln | Gly | Val | Thr | Gln |
|     |     |     | 820 |     |     |     |     | 825 |     |     |     |     | 830 |     |     |
| Val | Val | Leu | Lys | Gly | Ala | Pro | Gly | Gln | Pro | Gly | Thr | Ile | Leu | Arg | Thr |
|     |     |     | 835 |     |     |     |     | 840 |     |     |     |     | 845 |     |     |
| Val | Pro | Met | Gly | Gly | Val | Arg | Leu | Val | Thr | Pro | Val | Thr | Val | Ser | Ala |
|     | 850 |     |     |     |     | 855 |     |     |     |     | 860 |     |     |     |     |
| Val | Lys | Pro | Ala | Val | Thr | Thr | Leu | Val | Val | Lys | Gly | Thr | Thr | Gly | Val |
| 865 |     |     |     |     | 870 |     |     |     |     | 875 |     |     |     |     | 880 |
| Thr | Thr | Leu | Gly | Thr | Val | Thr | Gly | Thr | Val | Ser | Thr | Ser | Leu | Ala | Gly |
|     |     |     |     | 885 |     |     |     |     | 890 |     |     |     |     | 895 |     |
| Ala | Gly | Gly | His | Ser | Thr | Ser | Ala | Ser | Leu | Ala | Thr | Pro | Ile | Thr | Thr |
|     |     |     |     | 900 |     |     |     |     | 905 |     |     |     |     | 910 |     |
| Leu | Gly | Thr | Ile | Ala | Thr | Leu | Ser | Ser | Gln | Val | Ile | Asn | Pro | Thr | Ala |
|     |     |     | 915 |     |     |     |     | 920 |     |     |     |     | 925 |     |     |
| Ile | Thr | Val | Ser | Ala | Ala | Gln | Thr | Thr | Leu | Thr | Ala | Ala | Gly | Gly | Leu |
|     |     |     | 930 |     |     |     |     | 935 |     |     |     |     | 940 |     |     |
| Thr | Thr | Pro | Thr | Ile | Thr | Met | Gln | Pro | Val | Ser | Gln | Pro | Thr | Gln | Val |
| 945 |     |     |     |     | 950 |     |     |     |     | 955 |     |     |     |     | 960 |
| Thr | Leu | Ile | Thr | Ala | Pro | Ser | Gly | Val | Glu | Ala | Gln | Pro | Val | His | Asp |
|     |     |     |     | 965 |     |     |     |     | 970 |     |     |     |     | 975 |     |
| Leu | Pro | Val | Ser | Ile | Leu | Ala | Ser | Pro | Thr | Thr | Glu | Gln | Pro | Thr | Ala |
|     |     |     | 980 |     |     |     |     | 985 |     |     |     |     | 990 |     |     |
| Thr | Val | Thr | Ile | Ala | Asp | Ser | Gly | Gln | Gly | Asp | Val | Gln | Pro | Gly | Thr |
|     |     |     | 995 |     |     |     | 1000 |     |     |     |     | 1005 |     |     |     |
| Val | Thr | Leu | Val | Cys | Ser | Asn | Pro | Pro | Cys | Glu | Thr | His | Glu | Thr | Gly |
|     |     |     | 1010 |     |     |     |     | 1015 |     |     |     |     | 1020 |     |     |
| Thr | Thr | Asn | Thr | Ala | Thr | Thr | Thr | Val | Val | Ala | Asn | Leu | Gly | Gly | His |
| 1025 |    |     |     |     | 1030 |    |     |     |     | 1035 |    |     |     |     | 1040 |
| Pro | Gln | Pro | Thr | Gln | Val | Gln | Phe | Val | Cys | Asp | Arg | Gln | Glu | Ala | Ala |
|     |     |     |     | 1045 |     |     |     |     | 1050 |     |     |     |     | 1055 |     |

```
Ala  Ser  Leu  Val  Thr  Ser  Thr  Val  Gly  Gln  Gln  Asn  Gly  Ser  Val  Val
               1060                1065                1070

Arg  Val  Cys  Ser  Asn  Pro  Pro  Cys  Glu  Thr  His  Glu  Thr  Gly  Thr  Thr
          1075                1080                1085

Asn  Thr  Ala  Thr  Thr  Ala  Thr  Ser  Asn  Met  Ala  Gly  Gln  His  Gly  Cys
     1090                1095                1100

Ser  Asn  Pro  Pro  Cys  Glu  Thr  His  Glu  Thr  Gly  Thr  Thr  Asn  Thr  Ala
1105           1110                1115                     1120

Thr  Thr  Ala  Met  Ser  Ser  Val  Gly  Ala  Asn  His  Gln  Arg  Asp  Ala  Arg
               1125                1130                1135

Arg  Ala  Cys  Ala  Ala  Gly  Thr  Pro  Ala  Val  Ile  Arg  Ile  Ser  Val  Ala
               1140                1145                1150

Thr  Gly  Ala  Leu  Glu  Ala  Ala  Gln  Gly  Ser  Lys  Ser  Gln  Cys  Gln  Thr
               1155                1160                1165

Arg  Gln  Thr  Ser  Ala  Thr  Ser  Thr  Thr  Met  Thr  Val  Met  Ala  Thr  Gly
     1170                1175                1180

Ala  Pro  Cys  Ser  Ala  Gly  Pro  Leu  Leu  Gly  Pro  Ser  Met  Ala  Arg  Glu
1185                1190                1195                     1200

Pro  Gly  Gly  Arg  Ser  Pro  Ala  Phe  Val  Gln  Leu  Ala  Pro  Leu  Ser  Ser
               1205                1210                1215

Lys  Val  Arg  Leu  Ser  Ser  Pro  Ser  Ile  Lys  Asp  Leu  Pro  Ala  Gly  Arg
               1220                1225                1230

His  Ser  His  Ala  Val  Ser  Thr  Ala  Ala  Met  Thr  Arg  Ser  Ser  Val  Gly
               1235                1240                1245

Ala  Gly  Glu  Pro  Arg  Met  Ala  Pro  Val  Cys  Glu  Ser  Leu  Gln  Gly  Gly
     1250                1255                1260

Ser  Pro  Ser  Thr  Thr  Val  Thr  Val  Thr  Ala  Leu  Glu  Ala  Leu  Leu  Cys
1265                1270                1275                     1280

Pro  Ser  Ala  Thr  Val  Thr  Gln  Val  Cys  Ser  Asn  Pro  Pro  Cys  Glu  Thr
               1285                1290                1295

His  Glu  Thr  Gly  Thr  Thr  Asn  Thr  Ala  Thr  Thr  Ser  Asn  Ala  Gly  Ser
               1300                1305                1310

Ala  Gln  Arg  Val  Cys  Ser  Asn  Pro  Pro  Cys  Glu  Thr  His  Glu  Thr  Gly
     1315                1320                1325

Thr  Thr  His  Thr  Ala  Thr  Thr  Ala  Thr  Ser  Asn  Gly  Gly  Thr  Gly  Gln
1330                1335                1340

Pro  Glu  Gly  Gly  Gln  Gln  Pro  Pro  Ala  Gly  Arg  Pro  Cys  Glu  Thr  His
1345                1350                1355                     1360

Gln  Thr  Thr  Ser  Thr  Gly  Thr  Thr  Met  Ser  Val  Ser  Val  Gly  Ala  Leu
               1365                1370                1375

Leu  Pro  Asp  Ala  Thr  Ser  Ser  His  Arg  Thr  Val  Glu  Ser  Gly  Leu  Glu
               1380                1385                1390

Val  Ala  Ala  Ala  Pro  Ser  Val  Thr  Pro  Gln  Ala  Gly  Thr  Ala  Leu  Leu
               1395                1400                1405

Ala  Pro  Phe  Pro  Thr  Gln  Arg  Val  Cys  Ser  Asn  Pro  Pro  Cys  Glu  Thr
     1410                1415                1420

His  Glu  Thr  Gly  Thr  Thr  His  Thr  Ala  Thr  Thr  Val  Thr  Ser  Asn  Met
1425                1430                1435                     1440

Ser  Ser  Asn  Gln  Asp  Pro  Pro  Ala  Ala  Ser  Asp  Gln  Gly  Glu  Val
               1445                1450                1455

Glu  Ser  Thr  Gln  Gly  Asp  Ser  Val  Asn  Ile  Thr  Ser  Ser  Ser  Ala  Ile
               1460                1465                1470

Thr  Thr  Thr  Val  Ser  Ser  Thr  Leu  Thr  Arg  Ala  Val  Thr  Thr  Val  Thr
     1475                1480                1485
```

```
Gln  Ser  Thr  Pro  Val  Pro  Gly  Pro  Ser  Val  Pro  Pro  Pro  Glu  Glu  Leu
     1490               1495                    1500

Gln  Val  Ser  Pro  Gly  Pro  Arg  Gln  Gln  Leu  Pro  Pro  Arg  Gln  Leu  Leu
1505                1510                    1515                              1520

Gln  Ser  Ala  Ser  Thr  Ala  Leu  Met  Gly  Glu  Ser  Ala  Glu  Val  Leu  Ser
                    1525                    1530                         1535

Ala  Ser  Gln  Thr  Pro  Glu  Leu  Pro  Ala  Ala  Val  Asp  Leu  Ser  Ser  Thr
               1540                    1545                         1550

Gly  Glu  Pro  Ser  Ser  Gly  Gln  Glu  Ser  Ala  Gly  Ser  Ala  Val  Val  Ala
               1555                    1560                    1565

Thr  Val  Val  Gln  Pro  Pro  Pro  Thr  Gln  Ser  Glu  Val  Asp  Gln
1570                    1575                    1580

Leu  Ser  Leu  Pro  Gln  Glu  Leu  Met  Ala  Glu  Ala  Gln  Ala  Gly  Thr  Thr
1585                    1590                    1595                         1600

Thr  Leu  Met  Val  Thr  Gly  Leu  Thr  Pro  Glu  Glu  Leu  Ala  Val  Thr  Ala
                    1605                    1610                         1615

Ala  Ala  Glu  Ala  Ala  Ala  Gln  Ala  Ala  Ala  Thr  Glu  Glu  Ala  Gln  Ala
               1620                    1625                         1630

Leu  Ala  Ile  Gln  Ala  Val  Leu  Gln  Ala  Ala  Gln  Gln  Ala  Val  Met  Gly
          1635                    1640                         1645

Thr  Gly  Glu  Pro  Met  Asp  Thr  Ser  Glu  Ala  Ala  Ala  Thr  Val  Thr  Gln
          1650                    1655                         1660

Ala  Glu  Leu  Gly  His  Leu  Ser  Ala  Glu  Gly  Gln  Glu  Gly  Gln  Ala  Thr
1665                    1670                    1675                         1680

Thr  Ile  Pro  Ile  Val  Leu  Thr  Gln  Gln  Glu  Leu  Ala  Ala  Leu  Val  Gln
                    1685                    1690                         1695

Gln  Gln  Gln  Leu  Gln  Glu  Ala  Gln  Ala  Gln  Gln  Gln  His  His  His  Leu
               1700                    1705                         1710

Pro  Thr  Glu  Ala  Leu  Ala  Pro  Ala  Asp  Ser  Leu  Asn  Asp  Pro  Ala  Ile
          1715                    1720                         1725

Glu  Ser  Asn  Cys  Leu  Asn  Glu  Leu  Ala  Gly  Thr  Val  Pro  Ser  Thr  Val
     1730                    1735                         1740

Ala  Leu  Leu  Pro  Ser  Thr  Ala  Thr  Glu  Ser  Leu  Ala  Pro  Ser  Asn  Thr
1745                    1750                    1755                         1760

Phe  Val  Ala  Pro  Gln  Pro  Val  Val  Val  Ala  Ser  Pro  Ala  Lys  Leu  Gln
               1765                    1770                         1775

Ala  Ala  Ala  Thr  Leu  Thr  Glu  Val  Ala  Asn  Gly  Ile  Glu  Ser  Leu  Gly
               1780                    1785                         1790

Val  Lys  Pro  Asp  Leu  Pro  Pro  Pro  Ser  Lys  Ala  Pro  Met  Lys  Lys
          1795                    1800                    1805

Glu  Asn  Gln  Trp  Phe  Asp  Val  Gly  Val  Ile  Lys  Gly  Thr  Asn  Val  Met
     1810                    1815                    1820

Val  Thr  His  Tyr  Phe  Leu  Pro  Pro  Asp  Asp  Ala  Val  Pro  Ser  Asp  Asp
1825                    1830                    1835                         1840

Asp  Leu  Gly  Thr  Val  Pro  Asp  Tyr  Asn  Gln  Leu  Lys  Lys  Gln  Glu  Leu
               1845                    1850                         1855

Gln  Pro  Gly  Thr  Ala  Tyr  Lys  Phe  Arg  Val  Ala  Gly  Ile  Asn  Ala  Cys
          1860                    1865                         1870

Gly  Arg  Gly  Pro  Phe  Ser  Glu  Ile  Ser  Ala  Phe  Lys  Thr  Cys  Leu  Pro
          1875                    1880                         1885

Gly  Phe  Pro  Gly  Ala  Pro  Cys  Ala  Ile  Lys  Ile  Ser  Lys  Ser  Pro  Asp
          1890                    1895                         1900

Gly  Ala  His  Leu  Thr  Trp  Glu  Pro  Pro  Ser  Val  Thr  Ser  Gly  Lys  Ile
```

```
           1905                    1910                     1915                      1920
     Ile  Glu  Tyr  Ser  Val  Tyr  Leu  Ala  Ile  Gln  Ser  Ser  Gln  Ala  Gly  Gly
                         1925                    1930                     1935
     Glu  Leu  Lys  Ser  Ser  Thr  Pro  Ala  Gln  Leu  Ala  Phe  Met  Arg  Val  Tyr
                         1940                    1945                     1950
     Cys  Gly  Pro  Ser  Pro  Ser  Cys  Leu  Val  Gln  Ser  Ser  Ser  Leu  Ser  Asn
                         1955                    1960                     1965
     Ala  His  Ile  Asp  Tyr  Thr  Thr  Lys  Pro  Ala  Ile  Ile  Phe  Arg  Ile  Ala
          1970                    1975                     1980
     Ala  Arg  Asn  Glu  Lys  Gly  Tyr  Gly  Pro  Ala  Thr  Gln  Val  Arg  Trp  Leu
     1985                    1990                     1995                         2000
     Gln  Glu  Thr  Ser  Lys  Asp  Ser  Ser  Gly  Thr  Lys  Pro  Ala  Asn  Lys  Arg
                         2005                    2010                     2015
     Pro  Met  Ser  Ser  Pro  Glu  Met  Lys  Ser  Ala  Pro  Lys  Lys  Ser  Lys  Ala
                         2020                    2025                     2030
     Asp  Gly  Gln
               2035
```

( 2 ) INFORMATION FOR SEQ ID NO:6:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
     Thr  Leu  Val  Cys  Ser  Asn  Pro  Pro  Cys  Glu  Thr  His  Glu  Thr  Gly  Thr
     1                    5                         10                         15
     Thr  Asn  Thr  Ala  Thr  Thr  Thr  Val  Val  Ala
                    20                    25
```

( 2 ) INFORMATION FOR SEQ ID NO:7:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
     Val  Arg  Val  Cys  Ser  Asn  Pro  Pro  Cys  Glu  Thr  His  Glu  Thr  Gly  Thr
     1                    5                         10                         15
     Thr  Asn  Thr  Ala  Thr  Thr  Ala  Thr  Ser  Asn
                    20                    25
```

( 2 ) INFORMATION FOR SEQ ID NO:8:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
     Gln  His  Gly  Cys  Ser  Asn  Pro  Pro  Cys  Glu  Thr  His  Glu  Thr  Gly  Thr
     1                    5                         10                         15
```

Thr  Asn  Thr  Ala  Thr  Thr  Ala  Met  Ser  Ser
                            20                  25

(2) INFORMATION FOR SEQ ID NO:9:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Ala  Ala  Gln  Gly  Ser  Lys  Ser  Gln  Cys  Gln  Thr  Arg  Gln  Thr  Ser  Ala
    1                   5                        10                       15

Thr  Ser  Thr  Thr  Met  Thr  Val  Met  Ala  Thr
                   20                  25

(2) INFORMATION FOR SEQ ID NO:10:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Thr  Gln  Val  Cys  Ser  Asn  Pro  Pro  Cys  Glu  Thr  His  Glu  Thr  Gly  Thr
    1                   5                        10                       15

Thr  Asn  Thr  Ala  Thr  Thr  Ser  Asn  Ala  Gly
                   20                  25

(2) INFORMATION FOR SEQ ID NO:11:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Gln  Arg  Val  Cys  Ser  Asn  Pro  Pro  Cys  Glu  Thr  His  Glu  Thr  Gly  Thr
    1                   5                        10                       15

Thr  His  Thr  Ala  Thr  Thr  Ala  Thr  Ser  Asn
                   20                  25

(2) INFORMATION FOR SEQ ID NO:12:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Gln  Gln  Pro  Pro  Ala  Gly  Arg  Pro  Cys  Glu  Thr  His  Gln  Thr  Thr  Ser
    1                   5                        10                       15

Thr  Gly  Thr  Thr  Met  Ser  Val  Ser  Val  Gly
                   20                  25

( 2 ) INFORMATION FOR SEQ ID NO:13:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Gln  Arg  Val  Cys  Ser  Asn  Pro  Pro  Cys  Glu  Thr  His  Glu  Thr  Gly  Thr
  1              5                         10                        15
Thr  His  Thr  Ala  Thr  Thr  Val  Thr  Ser  Asn
              20                        25
```

( 2 ) INFORMATION FOR SEQ ID NO:14:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Gln  Arg  Val  Cys  Ser  Asn  Pro  Pro  Cys  Glu  Thr  His  Glu  Thr  Gly  Thr
  1              5                         10                        15
Thr  Asn  Thr  Ala  Thr  Thr  Ala  Thr  Ser  Asn
              20                        25
```

( 2 ) INFORMATION FOR SEQ ID NO:15:

( i ) SEQUENCE CHARACTERISTICS:
        ( A ) LENGTH: 8252 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:15:

```
AGGCGGCTCA  AGATGGCGGC  TCCCAGGGCC  TCCCGCCCGA  GCTTGTAAGC  GGGAGCGCCC    60
GGACAAGTAG  TCGGGGCGAC  GGGACTCAGC  GGCCTCCAGC  TTCTTGAGCC  TAGGCGCTCG   120
ACAGTTTCGG  GCGGCTCTTG  CGGAGACGGG  GTGAGCGAGA  AGAAAGGGAA  GAGCCAAAGG   180
GAAGGAGGGC  AGTTAAGATG  GCGGCCTCCA  TGGAGTCGTC  TACCGCTGTG  TGAGAAACCG   240
CTTCTCCGTG  AGAGCTGCCT  TAGACGAAAG  GGGGTGTGTG  AAAGGAATTG  AGGGGCTCCC   300
TTCCCGCTTG  TTGACTTCTC  CCCACCGCAC  CCTTTCCCGG  AACTATGGCT  TCGGCCGTGT   360
CGCCCGCCAA  CTTGCCAGCG  GTGCTTCTGC  AGCCCGCTG   GAAGCGAGTG  GTGGGCTGGT   420
CGGGTCCGGT  GCCACGGCCC  CGCCACGGCC  ACCGCGCCGT  GGCCATCAAG  GAGCTCATCG   480
TGGTGTTTGG  CGGCGGCAAC  GAGGGAATAG  TGGACGAACT  GCACGTGTAC  AACACGGCAA   540
CCAACCAGTG  GTTCATCCCA  GCCGTGAGGG  GGGACATTCC  CCCTGGGTGT  GCAGCCTATG   600
GCTTCGTGTG  TGACGGGACT  CGCCTCCTGG  TGTTTGGTGG  GATGGTGGAG  TATGGGAAAT   660
ACAGCAATGA  CCTCTACGAA  CTCCAGGCGA  GCCGGTGGGA  GTGGAAGAGA  CTCAAAGCAA   720
AGACGCCCAA  AAACGGGCCC  CCTCCGTGTC  CTCGACTCGG  GCACAGCTTC  TCCCTTGTGG   780
GCAACAAATG  CTACCTGTTT  GGGGTCTGG   CCAATGATAG  CGAGGACCCA  AAGAACAACA   840
TTCCAAGGTA  CCTGAATGAC  TTATATATCC  TGGAATTACG  GCCAGGCTCT  GGAGTGGTAG   900
```

-continued

| | | | | | |
|---|---|---|---|---|---|
| CCTGGGACAT | TCCCATCACT | TACGGGGTCC | TACCACCACC | CCGGGAGTCA | CATACTGCCG | 960
| TGGTCTACAC | CGAAAAAGAC | AATAAGAAGT | CCAAGCTGGT | GATCTACGGC | GGGATGAGTG | 1020
| GCTGCAGGCT | GGGGGACCTG | TGGACCCTAG | ATATTGACAC | CCTGACGTGG | AATAAGCCCA | 1080
| GTCTCAGCGG | GGTGGCGCCT | CTTCCTCGCA | GTCTCCACTC | GGCAACCACC | ATCGGAAATA | 1140
| AAATGTACGT | GTTTGGTGGC | TGGGTGCCTC | TCGTCATGGA | TGACGTCAAA | GTGGCCACAC | 1200
| ACGAGAAGGA | GTGGAAGTGT | ACCAACACGC | TGGCTTGTCT | CAACCTGGAT | ACCATGGCCT | 1260
| GGGAGACCAT | CCTGATGGAT | ACACTGGAGG | ACAACATCCC | CCGTGCTCGG | GCTGGCCACT | 1320
| GCGCAGTCGC | CATCAACACC | CGCCTGTACA | TTTGGAGTGG | GCGTGACGGC | TACCGCAAGG | 1380
| CCTGGAACAA | CCAGGTCTGC | TGCAAGGACC | TCTGGTACCT | AGAGACAGAA | AAGCCACCAC | 1440
| CCCCAGCCCG | AGTACAACTG | GTACGCGCCA | ACACCAACTC | CCTGGAGGTG | AGCTGGGGGG | 1500
| CAGTGGCAAC | AGCCGACAGC | TACCTTCTCC | AGCTCCAGAA | ATATGACATT | CCTGCCACGG | 1560
| CTGCTACTGC | CACCTCCCCT | ACACCCAATC | CGGTCCCATC | TGTGCCTGCC | AACCCTCCCA | 1620
| AGAGCCCTGC | CCCAGCAGCA | GCCGCACCTG | CTGTGCAGCC | GCTGACCCAA | GTAGGCATCA | 1680
| CGCTCCTGCC | CCAGGCTGCC | CCCGCACCCC | CGACCACCAC | CACCATCCAG | GTCTTGCCAA | 1740
| CGGTGCCTGG | CAGCTCCATT | TCTGTGCCCA | CCGCAGCCAG | GACTCAAGGT | GTCCCTGCTG | 1800
| TTCTCAAAGT | GACCGGTCCT | CAGGCTACAA | CAGGAACTCC | ATTGGTCACC | ATGCGACCTG | 1860
| CCAGCCAGGC | TGGGAAAGCC | CCTGTCACCG | TGACCTCCCT | TCCCGCCGGA | GTGCGGATGG | 1920
| TTGTGCCAAC | ACAGAGTGCC | CAGGGAACGG | TGATTGGCAG | TAGCCCACAG | ATGAGTGGGA | 1980
| TGGCCGCACT | GGCCGCTGCG | GCCGCTGCCA | CCCAGAAGAT | CCCCCCTTCC | TCGGCACCCA | 2040
| CGGTGCTGAG | TGTCCCAGCG | GGTACCACCA | TCGTGAAGAC | CATGGCTGTG | ACACCTGGCA | 2100
| CTACCACCCT | CCCAGCCACT | GTGAAGGTGG | CCTCCTCGCC | AGTCATGGTG | AGCAACCCTG | 2160
| CCACTCGCAT | GCTGAAGACT | GCAGCCGCCC | AGGTGGGGAC | ATCGGTTTCC | TCCGCCACCA | 2220
| ACACGTCTAC | CCGCCCTATC | ATCACAGTGC | ACAAGTCAGG | CACTGTGACA | GTGGCCCAGC | 2280
| AAGCCCAGGT | GGTGACCACA | GTTGTGGGCG | GGGTCACCAA | GACCATCACC | CTGGTGAAGA | 2340
| GCCCCATCTC | TGTCCCAGGA | GGCAGTGCTC | TGATTTCCAA | TCTGGGCAAA | GTGATGTCGG | 2400
| TGGTCCAGAC | CAAACCAGTT | CAGACTTCAG | CAGTCACAGG | CCAGGCGTCC | ACGGGTCCTG | 2460
| TGACTCAGAT | CATCCAGACC | AAAGGGCCCC | TGCCAGCGGG | AACAATCCTG | AAGCTGGTGA | 2520
| CCTCAGCAGA | TGGCAAGCCC | ACCACCATCA | TCACTACCAC | GCAGGCCAGT | GGGGCGGGGA | 2580
| CCAAGCCCAC | CATCCTGGGC | ATCAGCAGCG | TCTCCCCCAG | TACCACCAAG | CCCGGCACGA | 2640
| CCACCATCAT | CAAAACCATC | CCCATGTCGG | CCATCATCAC | CAGGCGGGC | GCCACGGGTG | 2700
| TGACCAGCAG | TCCTGGCATC | AAGTCCCCCA | TCACCATCAT | CACCACCAAG | GTGATGACTT | 2760
| CAGGAACTGG | AGCACCTGCG | AAAATCATCA | CTGCTGTCCC | CAAAATTGCC | ACTGGCCACG | 2820
| GGCAGCAGGG | AGTGACCCAG | GTGGTGCTTA | AGGGGCCCC | GGGACAGCCA | GGCACCATCC | 2880
| TCCGCACTGT | GCCCATGGGG | GGTGTTCGCC | TGGTCACACC | CGTCACCGTC | TCCGCCGTCA | 2940
| AGCCAGCCGT | CACCACGTTG | GTTGTGAAAG | GCACCACAGG | TGTCACGACC | CTAGGCACAG | 3000
| TGACAGGCAC | CGTCTCCACC | AGCCTTGCCG | GGGCGGGGG | CCACAGCACT | AGTGCTTCCC | 3060
| TGGCCACGCC | CATCACCACC | TTGGGCACCA | TTGCCACCCT | CTCAAGCCAG | GTGATCAACC | 3120
| CCACTGCCAT | CACTGTGTCG | GCCGCACAGA | CCACGCTGAC | AGCGGCAGGC | GGGCTCACAA | 3180
| CCCCAACCAT | CACCATGCAG | CCCGTGTCCC | AGCCCACCCA | GGTAACTCTG | ATCACGGCAC | 3240
| CTAGTGGGGT | GGAGGCCCAG | CCTGTGCATG | ACCTCCCTGT | GTCCATTCTG | GCCTCCCCGA | 3300

| | | | | | | |
|---|---|---|---|---|---|---|
| CTACAGAACA | GCCCACCGCC | ACAGTTACCA | TCGCCGACTC | AGGCCAGGGT | GATGTGCAGC | 3360 |
| CTGGCACTGT | CACCTTGGTG | TGCTCCAACC | CACCCTGTGA | GACCCACGAG | ACTGGCACCA | 3420 |
| CCAACACGGC | CACCACTACT | GTTGTGGCTA | ACCTTGGGGG | ACACCCCCAG | CCCACCCAAG | 3480 |
| TGCAGTTCGT | CTGTGACAGA | CAGGAGGCAG | CTGCTTCTCT | TGTGACCTCG | ACTGTGGGCC | 3540 |
| AGCAGAATGG | TAGCGTGGTC | CGAGTCTGTT | CGAACCCGCC | CTGCGAGACC | CACGAGACGG | 3600 |
| GCACCACCAA | CACCGCCACC | ACCGCCACCT | CCAACATGGC | CGGGCAGCAT | GGCTGCTCAA | 3660 |
| ACCCACCCTG | CGAGACCCAC | GAGACGGGCA | CCACCAACAC | TGCCACTACA | GCCATGTCGA | 3720 |
| GCGTCGGCGC | CAACCACCAG | CGAGATGCCC | GTCGGCCTG | TGCAGCTGGC | ACCCCTGCCG | 3780 |
| TGATCCGGAT | CAGTGTGGCC | ACTGGGGCGC | TGGAGGCAGC | CCAGGGCTCT | AAGTCCCAGT | 3840 |
| GCCAAACCCG | CCAGACCAGC | GCGACCAGCA | CCACCATGAC | TGTGATGGCC | ACCGGGGCCC | 3900 |
| CGTGCTCGGC | CGGCCCACTC | CTTGGGCCGA | GCATGGCACG | GGAGCCCGGG | GGCCGCAGCC | 3960 |
| CTGCTTTTGT | GCAGTTGGCC | CCTCTGAGCA | GCAAAGTCAG | GCTGAGCAGC | CAAGCATTA | 4020 |
| AGGACCTTCC | TGCGGGGCGC | CACAGCCATG | CGGTCAGCAC | CGCTGCCATG | ACCCGTTCCA | 4080 |
| GCGTGGGTGC | TGGGGAGCCC | CGCATGGCAC | CTGTGTGCGA | GAGCCTCCAG | GGTGGCTCGC | 4140 |
| CCAGCACCAC | AGTGACTGTG | ACAGCCCTGG | AGGCACTGCT | GTGCCCCTCG | GCCACCGTGA | 4200 |
| CCCAAGTCTG | CTCCAACCCA | CCATGTGAGA | CCCACGAGAC | AGGCACCACC | AACACCGCCA | 4260 |
| CTACCTCGAA | TGCAGGCAGC | GCCCAGAGGG | TGTGCTCCAA | CCCGCCATGC | GAGACCCACG | 4320 |
| AGACGGGCAC | CACCCACACG | GCCACCACCG | CTACTTCAAA | CGGGGGCACG | GGCCAGCCCG | 4380 |
| AGGGTGGGCA | GCAGCCCCCT | GCTGGTCGCC | CCTGTGAGAC | ACACCAGACC | ACTTCCACTG | 4440 |
| GCACCACCAT | GTCGGTCAGC | GTGGGTGCCC | TGCTTCCCGA | CGCCACTTCT | TCCCACAGGA | 4500 |
| CCGTGGAGTC | TGGCCTAGAG | GTGGCGGCGG | CACCCAGCGT | CACCCCCCAG | GCTGGCACCG | 4560 |
| CGCTGCTGGC | TCCTTTCCCA | ACACAGAGGG | TGTGCTCCAA | CCCCCCTGT | GAGACCCACG | 4620 |
| AGACGGGCAC | CACTCACACG | GCCACCACTG | TCACTTCCAA | CATGAGTTCA | AACCAAGACC | 4680 |
| CCCCACCTGC | TGCCAGCGAT | CAGGGAGAGG | TGGAGAGCAC | CCAGGGCGAC | AGCGTGAACA | 4740 |
| TCACCAGCTC | CAGTGCCATC | ACGACAACCG | TGTCCTCCAC | ACTGACGCGG | GCTGTGACCA | 4800 |
| CCGTGACGCA | GTCCACACCG | GTCCCGGGCC | CCTCTGTGCC | GCCCCCAGAG | GAACTCCAGG | 4860 |
| TGTCGCCAGG | TCCTCGCCAG | CAGCTGCCGC | CACGGCAGCT | TCTGCAGTCG | GCTTCCACAG | 4920 |
| CCCTGATGGG | GGAGTCCGCC | GAGGTCCTGT | CAGCCTCCCA | GACCCTGAG | CTCCCGGCCG | 4980 |
| CCGTGGATCT | GAGCAGCACA | GGGGAGCCAT | CTTCGGGCCA | GGAGTCTGCC | GGCTCTGCGG | 5040 |
| TGGTGGCCAC | TGTGGTGGTC | CAGCCACCCC | CACCCACACA | GTCCGAAGTA | GACCAGTTAT | 5100 |
| CACTTCCCCA | AGAGCTAATG | GCCGAGGCCC | AAGCTGGCAC | CACCACCCTC | ATGGTAACGG | 5160 |
| GGCTCACCCC | CGAGGAGCTG | GCAGTGACGG | CTGCTGCAGA | AGCAGCTGCC | CAGGCCGCAG | 5220 |
| CCACGGAGGA | AGCCCAGGCC | CTGGCCATCC | AGGCGGTGCT | CCAGGCCGCG | CAGCAGGCCG | 5280 |
| TCATGGGCAC | CGGCGAGCCC | ATGGACACCT | CCGAGGCAGC | AGCAACCGTG | ACTCAGGCGG | 5340 |
| AGCTGGGGCA | CCTGTCGGCC | GAGGGTCAGG | AGGGCCAGGC | CACCACCATA | CCCATTGTGC | 5400 |
| TGACACAGCA | GGAGCTGGCT | GCCCTGGTGC | AGCAGCAGCA | GCTGCAGGAG | GCCCAGGCCC | 5460 |
| AGCAGCAGCA | TCACCACCTC | CCCACTGAGG | CCCTGGCCCC | TGCCGACAGT | CTCAACGACC | 5520 |
| CAGCCATTGA | GAGCAATTGC | CTCAATGAGC | TGGCCGGCAC | GGTCCCCAGC | ACTGTGGCGC | 5580 |
| TGCTGCCCTC | AACGGCCACT | GAGAGCCTGG | CTCCATCCAA | CACATTTGTG | GCCCCCAGC | 5640 |
| CGGTTGTGGT | GGCCAGCCCA | GCCAAGCTGC | AGGCTGCAGC | TACCCTGACC | GAAGTGGCCA | 5700 |

```
ATGGCATCGA  GTCCCTGGGT  GTGAAGCCAG  ACCTGCCGCC  CCCACCCAGC  AAAGCCCCCA   5760
TGAAGAAGGA  AAACCAGTGG  TTTGATGTGG  GAGTCATTAA  GGGCACCAAT  GTAATGGTGA   5820
CACACTATTT  CCTGCCACCA  GATGATGCTG  TCCCATCAGA  CGATGATTTG  GGCACCGTCC   5880
CTGACTATAA  CCAGCTGAAG  AAGCAGGAGC  TGCAGCCAGG  CACAGCCTAT  AAGTTCGTG    5940
TTGCCGGAAT  CAATGCCTGT  GGCCGGGGGC  CCTTCAGCGA  AATCTCAGCC  TTTAAGACGT   6000
GCCTGCCTGG  TTTCCAGGG   GCCCCTTGTG  CCATTAAAAT  CAGCAAAAGT  CCGGATGGTG   6060
CTCACCTCAC  CTGGGAGCCA  CCCTCTGTGA  CCTCCGGCAA  GATTATCGAG  TACTCCGTGT   6120
ACCTGGCCAT  CCAGAGCTCA  CAGGCTGGGG  GCGAGCTCAA  GAGCTCCACC  CCGGCCCAGC   6180
TGGCCTTCAT  GCGGGTGTAC  TGTGGGCCCA  GCCCCTCCTG  CCTGGTGCAG  TCCTCCAGCC   6240
TTTCCAACGC  CCACATCGAC  TACACCACCA  AGCCCGCCAT  CATCTTCCGC  ATCGCCGCCC   6300
GCAATGAGAA  GGGCTATGGC  CCGGCCACAC  AAGTGAGGTG  GCTGCAGGAA  ACCAGTAAAG   6360
ACAGCTCTGG  CACCAAGCCA  GCCAACAAGC  GGCCCATGTC  CTCTCCAGAA  ATGAAATCTG   6420
CTCCAAAGAA  ATCTAAGGCC  GATGGTCAGT  GAGAGGAAGC  TGACTAGCCC  CTGGATTCTT   6480
CTCCAGACCC  CCCTGCTTCA  GGAACACCCG  CCAGGGCCCA  CCCTCCCAC   CCCGTCCAG    6540
CATTCGCACT  TCACCCTCGC  GAGCCGCTGT  TCACTCCTCT  CCCCTTTCTC  TTTCTCTCTG   6600
TTTTTAAAAT  AATCTAAAGA  AAGCACATTT  TACCATTGCT  GTTGGGAGGA  AGCAGAGGCA   6660
GATGGGAAAG  CAGAGAGAGG  AGCGCGCTTC  CTTTCCTCCC  CGCTGCCGCC  CACCCTGGGG   6720
AGAGACTTTT  GCGGGGAGGG  AAGGCGGAGC  TGAGGACAGC  CAGCTCCGCC  CTCCCAAGGC   6780
TGTGCGTTCC  TGAGGGCCAG  GTCGGGGGCA  GGCATGGAGG  GGAGGAAAGG  CGTCCCTCTT   6840
GGCCCTCCCC  AGAGTGGCTT  TCCTGGCACC  CTGGCCTGGG  TGTCTGGTTC  TGTTTCTTT    6900
TCTTCCCCTT  GTGTTTCCAG  TCACCTAACT  TCCCTTCCTC  AGGCTCCCCC  GGCCCACCCT   6960
GCTCAGTGAC  CCCACAGGAA  GCTTACACAT  TTTCTCAGAG  GCCTTTGTGC  TCCACCTCT    7020
TCTACCCTCC  CCCTCTTCTT  TCCCATTTTA  AAAAGAAAA   GAAGGAAAAA  GAAAAAGGG    7080
GCAAGGAGCC  CCGCGGCGGC  CTGGGCAGCG  CCTGTGCAGA  CCTCCCTGCA  GGCCGCACTG   7140
CCAACTGCTG  CATTTGTTGT  GTTTTTAGG   TTGCAATTGG  TGAAGTTCAC  ACTTTCATTG   7200
TAATTTTAGC  GTGTGGGGTT  TTGTCCCTTT  TTTGTTGTTG  TTAGCTGTGT  ACAGAATGTG   7260
TAACCTTTTT  TCTTTTCTCT  TTTTTTTGTT  TTGTTTTGTT  TTGTTTTGTT  TTTTACTTT    7320
TTTCTTCTTG  GCTAATTCTT  GGCAGGGATC  TTTCTGGAGG  AAAAGCTGGG  GCCAGCCAGG   7380
GCAGGAGAGG  TGTGAAATCT  GCCACGAGGG  GCCTGCTGTT  TGCCACCCAG  CCCAACTTCC   7440
TGTTGCTGGC  CCCTGCCCTC  TGCCCTTTTG  CCTGTCCTCA  GGCCGCTGGA  ACAAAGGAAG   7500
GACAGCTCAT  TCCTCATGGG  CGATCACTCC  GCATCTATAG  GGTCGAGCCT  AGGGGAGCTT   7560
GAGGGAGGGC  TGGGGCCTCC  TTGTCCTGGA  TTTCCAGCTC  TCCCCATCCC  CCCTCCCTGA   7620
GCACCACCGG  CACCGCCTCC  CAAACAGGGC  TGCTGGTTTC  CGCAGCCACT  GCTCCACCTC   7680
CCCCAAATCG  TCATGGAAAG  GGTGGAGATG  GAGGGGAACC  AGGCGTCCTT  GGAGGCAGCT   7740
TGGGAGGGTG  ACTGTGTAGT  GTCACCCACA  AGGGAGGCTA  GGGCAATGGA  GCAGGCCACC   7800
AGCAGCAGCT  GTGCAGCATG  GAACTCAGGC  CAGGCTCCGA  GGCTGGGGA   TCTGCTTGGA   7860
GTTTTCTGCC  CCCCACCCCA  AACTTCTGTC  GAGGAGCAAG  GCTTGCCAGC  AAGTCAGAAG   7920
GATTTGAACC  GAGCAGCCAA  TCTTTCCAGC  CCTCCCCTAC  CGACCTCTGC  CTGGAGACGC   7980
AGCAGCCTGT  GTCCTCCAGG  GCCTCTGGTT  TGTTGTATTA  TAGTATATTT  CGCTGTGGAA   8040
AATGTCACGT  TTAGTCACCT  TGGAGCCCAC  TCACCTGGTC  CTGTTGTTTT  ACCCCATCCC   8100
```

| | | | | | | |
|---|---|---|---|---|---|---|
| TTCTCTCGCG | CGCCTATTGA | TTTGTTTCTG | AGGAGAGTAC | ACCGTTCACT | ATTGTAGAGT | 8160 |
| AACCCCTGTG | ACTCAATATT | ACCATAGTGC | GATGTCGTTT | TGTGCTATTT | TGAACAATTA | 8220 |
| AAAGACTTTT | TTTGAAATAA | AAAAAAAAA | AA | | | 8252 |

What is claimed is:

1. A method of screening for a compound which modulates Herpes Simplex Virus (HSV) transcription complex formation, said method comprising the steps of:

adding a prospective agent to a mixture comprising HSV transcription components including recombinantly produced Host Cell Factor (SEQ ID NO: 5) or polypeptide which consists of a sequence of six or more consecutive amino acids of Host Cell Factor, which polypeptide specifically binds a transcription factor, and said transcription factor; and, comparing the in vitro association of said components before and after said adding step, wherein a difference between said in vitro association before and after said adding step identifies said prospective agent as a lead pharmaceutical compound which modulates the formation of a Herpes Simplex Virus transcription complex.

2. A method according to claim 1 wherein said mixture further comprises a nucleic acid and said transcription factor is VP16.

* * * * *